United States Patent
Sinha et al.

(10) Patent No.: US 9,617,210 B2
(45) Date of Patent: Apr. 11, 2017

(54) PYRROLE DERIVATIVES AS ALPHA 7 NACHR MODULATORS

(71) Applicant: Lupin Limited, Mumbai, Maharashtra (IN)

(72) Inventors: Neelima Sinha, Pune (IN); Navnath Popat Karche, Pune (IN); Shridhar Keshav Adurkar, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 21 days.

(21) Appl. No.: 14/655,476

(22) PCT Filed: Mar. 12, 2014

(86) PCT No.: PCT/IB2014/059674
§ 371 (c)(1),
(2) Date: Jun. 25, 2015

(87) PCT Pub. No.: WO2014/141091
PCT Pub. Date: Sep. 18, 2014

(65) Prior Publication Data
US 2015/0344422 A1    Dec. 3, 2015

(30) Foreign Application Priority Data

Mar. 13, 2013   (IN) .......................... 754/MUM/2013

(51) Int. Cl.
| | |
|---|---|
| *C07D 207/323* | (2006.01) |
| *A61K 45/06* | (2006.01) |
| *A61K 31/401* | (2006.01) |
| *C07D 401/04* | (2006.01) |
| *C07D 403/06* | (2006.01) |
| *C07D 207/34* | (2006.01) |

(52) U.S. Cl.
CPC ........ *C07D 207/323* (2013.01); *A61K 31/401* (2013.01); *A61K 45/06* (2013.01); *C07D 207/34* (2013.01); *C07D 401/04* (2013.01); *C07D 403/06* (2013.01)

(58) Field of Classification Search
None
See application file for complete search history.

(56) References Cited

U.S. PATENT DOCUMENTS

| | | |
|---|---|---|
| 7,683,084 B2 | 3/2010 | Faghih et al. |
| 7,741,364 B2 | 6/2010 | Faghih et al. |
| 9,072,731 B2 | 7/2015 | Sinha et al. |
| 9,393,247 B2 | 7/2016 | Sinha et al. |
| 2006/0142349 A1 | 6/2006 | Hurst et al. |
| 2007/0142450 A1 | 6/2007 | Dahl et al. |
| 2009/0253691 A1 | 10/2009 | Thuring et al. |
| 2010/0190819 A1 | 7/2010 | Kanner |
| 2010/0222398 A1 | 9/2010 | Nardi et al. |
| 2010/0227869 A1 | 9/2010 | Peters et al. |
| 2010/0240707 A1 | 9/2010 | Thuring et al. |

FOREIGN PATENT DOCUMENTS

| | | |
|---|---|---|
| EP | 1866314 B1 | 9/2010 |
| WO | WO 2007/031440 A2 | 3/2007 |
| WO | WO 2008/002974 A1 | 1/2008 |
| WO | WO 2009/043780 A1 | 4/2009 |
| WO | WO 2009/043784 A1 | 4/2009 |
| WO | WO 2009/115547 A1 | 9/2009 |
| WO | WO 2009/127678 A1 | 10/2009 |

(Continued)

OTHER PUBLICATIONS

Jones et al., Muscarinic and Nicotinic Acetylcholine Receptor Agonists and Allosteric Modulators for the Treatment of Schizophrenia. Neuropsychopharmacology, 2012, 37, 16-42.*

Decker et al., The therapeutic potential of nicotinic acetylcholine receptor agonists for pain control. Expert Opinion on Investigational Drugs, 2001, 10, 1819-1830.*

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

European Patent Office, International Search Report in corresponding International Application No. PCT/IB2014/059674, mailed May 21, 2014.

Albuquerque, E.X., et al., "Modulation of Nicotinic Receptor Activity in the Central Nervous System: A Novel Approach to the Treatment of Alzheimer Disease," *Alzheimer Disease and Associated Disorders*, vol. 15, Suppl. 1, pp. S19-S25 (2001).

(Continued)

*Primary Examiner* — Matthew Coughlin
*Assistant Examiner* — Po-Chih Chen
(74) *Attorney, Agent, or Firm* — Leydig, Voit & Mayer, Ltd.

(57) ABSTRACT

Disclosed are compounds of the Formula (I), wherein $R^1$, $R^2$, $R^3$, $R^4$, $R^5$, $R^6$, $R^7$ and m are as described herein, as modulators of the nicotinic acetylcholine receptors, particularly the α7 subtype, their tautomeric forms, stereoisomers, and their pharmaceutically acceptable salts, pharmaceutical compositions thereof, and combinations thereof with suitable other medicaments. Also disclosed are a process of preparation of the compounds and the intended uses thereof in therapy, particularly in the prophylaxis and/or treatment of disorders such as Alzheimer's disease, mild cognitive impairment, and senile dementia.

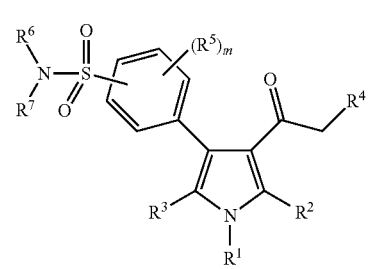

20 Claims, No Drawings

(56) References Cited

FOREIGN PATENT DOCUMENTS

| | | |
|---|---|---|
| WO | WO 2009/127679 A1 | 10/2009 |
| WO | WO 2009/135944 A1 | 11/2009 |
| WO | WO 2009/145996 A2 | 12/2009 |
| WO | WO 2010/130768 A1 | 11/2010 |
| WO | WO 2011/036167 A1 | 3/2011 |
| WO | WO 2011/064288 A1 | 6/2011 |
| WO | WO 2012/104782 A1 | 8/2012 |
| WO | WO 2012/114285 A9 | 8/2012 |
| WO | WO 2012/131576 A1 | 10/2012 |
| WO | WO 2013/005153 A1 | 1/2013 |
| WO | WO 2013/132380 A1 | 9/2013 |
| WO | WO 2014/111839 A1 | 7/2014 |

OTHER PUBLICATIONS

Alkondon, Manickavasagom, et al., "α7 Nicotinic acetylcholine receptors and modulation of gabaergic synaptic transmission in the hippocampus," *European Journal of Pharmacology*, vol. 393, pp. 59-67 (2000).

Arias, Hugo R., et al., "Role of non-neuronal nicotinic acetylcholine receptors in angiogenesis," *The International Journal of Biochemistry & Cell Biology*, vol. 41, pp. 1441-1451 (2009).

Berge, Stephen M., et al., "Pharmaceutical Salts," Review Article from *Journal of Pharmaceutical Sciences*, vol. 66, No. 1, pp. 1-19 (Jan. 1977).

Bitner, Robert S., et al., "Broad-Spectrum Efficacy across Cognitive Domains by α7 Nicotinic Acetylcholine Receptor Agonism Correlates with Activation of ERK1/2 and CREB Phosphorylation Pathways," *The Journal of Neuroscience*, vol. 27, No. 39, pp. 10578-10587 (Sep. 26, 2007).

Boess, Frank G., et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," *The Journal of Pharmacology and Experimental Therapeutics*, vol. 321, No. 2, pp. 716-725 (2007).

Bruchfeld, A., et al., "Whole blood cytokine attenuation by cholinergic agonists ex vivo and relationship to vagus nerve activity in rheumatoid arthritis," *Journal of Internal Medicine*, vol. 268, No. 1, pp. 94-101 (Jul. 2010).

Calleja-Macias, Itzel E., "Cholinergic signaling through nicotinic acetylcholine receptors stimulates the proliferation of cervical cancer cells: An explanation for the molecular role of tobacco smoking in cervical carcinogenesis?," *International Journal of Cancer*, vol. 124, pp. 1090-1096 (2009).

Cannon, Tyrone D., "The inheritance of intermediate phenotypes for schizophrenia," *Current Opinion in Psychiatry*, vol. 18, pp. 135-140 (2005).

Carson, Robyn, et al., "Genetic Variation in the α7 Nicotinic Acetylcholine Receptor is Associated with Delusional Symptoms in Alzheimers's Disease," *NeuroMolecular Medicine*, vol. 10, pp. 377-384 (2008).

Chan, Wai Kit, et al., "Frontal cortical α7 and α4β2 nicotinic acetylcholine receptors in working and reference memory," *Neuropharmacology*, vol. 52, pp. 1641-1649 (2007).

Chen, Jiuxi, et al., "Approach to Synthesis of β-Enamino Ketones and Pyrroles Catalyzed by Gallium(III) Triflate Under Solvent-Free Conditions," *Synthetic Communications*, vol. 39, pp. 4180-1498 (2009).

Curzon, Peter, et al., "Antisense knockdown of the rat α7 nicotinic acetylcholine receptor produces spatial memory impairment," *Neuroscience Letters*, vol. 410, pp. 15-19 (2006).

Dajas-Bailador, Federico, et al., "Nicotinic acetylcholine receptors and the regulation of neuronal signalling," *TRENDS in Pharmacological Sciences*, vol. 25, No. 6, pp. 317-324 (Jun. 2004).

Damaj, M. Imad, et al., "The antinociceptive effects of α7 nicotinic agonists in an acute pain model," *Neuropharmacology*, vol. 39, pp. 2785-2791 (2000).

Decker, Michael W., et al., "The therapeutic potential of nicotinic acetylcholine receptor agonists for pain control," *Expert Opinion on Investigational Drugs*, vol. 10, No. 10, pp. 1819-1830 (2001).

Deluca, Patrick P., et al., "Parenteral Drug-Delivery Systems," *Pharmaceutics and Pharmacy Practice*, Chapter 8, J.B. Lippincott Company, Philadelphia, PA, pp. 238-250 (1982).

Deutsch, Stephen I., et al., "Progressive Worsening of Adaptive Functions in Down Syndrome May Be Mediated by Complexing of Soluble Aβ Peptides With the $α_7$ Nicotinic Acetylcholine Receptor: Therapeutic Implications," *Clinical Neuropharmacology*, vol. 26, No. 5, pp, 277-283 (2003).

Donnelly-Roberts, Diana L., et al., "ABT-594 [(R)-5-(2-Azetidinylmethoxy)-2-Chloropyridine]: A Novel, Orally Effective Analgesic Acting via Neuronal Nicotinic Acetylcholine Receptors: I. In Vitro Characterization," *The Journal of Pharmacology and Experimental Therapeutics*, vol. 285, No. 2, pp. 777-786 (1998).

Dunlop, John, et al., "Old and New Pharmacology: Positive Allosteric Modulation of the α7 Nicotinic Acetylcholine Receptor by the 5-Hydroxytryptamine$_{2B/C}$ Receptor Antagonist SB-206553 (3,5-Dihydro-5-methyl-N-3-pyridinylbenzo[1,2-b:4,5-b'] di pyrrole-1-(2H)-carboxamide)," *The Journal of Pharmacology and Experimental Therapeutics*, vol. 328, No. 3, pp. 766-776 (2009).

Duris, Kamil, et al, "α7 Nicotinic Acetylcholine Receptor Agonist PNU-282987 Attenuates Early Brain Injury in a Perforation Model of Subarachnoid Hemorrhage in Rats," *Stroke*, vol. 42. pp. 3530-3536 (2011).

Dvornikova, Elena, et al., "Synthesis of 2- and 3-Substituted N-Methylpyrroles," *Synlett*, vol. 7, pp. 1152-1153 (2002).

Ebbert, Jon O., et al., "Varenicline for smoking cessation: efficacy, safety, and treatment recommendations," *Patient Preference and Adherence*, vol. 4, pp. 355-362 (2010).

Envivo Pharmaceuticals, "EnVivo Reports Positive Results of Its EVP-6124 Clinical Bio-Marker Study in Schizophrenia Patients," Press Release (Jan. 12, 2009).

Faghih, Ramin, et al., "Discovery of 4-(5-(4-Chlorophenyl)-2-methyl-3-propionyl-1H-pyrrol-1-yl)benzenesulfonamide (A-867744) as a Novel Positive Allosteric Modulator of the α7 Nicotinic Acetylcholine Receptor," *Journal of Medicinal Chemistry*, vol. 52, pp. 3377-3384 (2009).

Fehér, Ágnes, et al., "Association between a Genetic Variant of the Alpha-7 Nicotinic Acetylcholine Receptor Subunit and Four Types of Dementia," *Dementia and Geriatric Cognitive Disorders*, vol. 28, pp. 56-62 (2009).

Freedman, Robert, et al., "Evidence in Postmortem Brain Tissue for Decreased Numbers of Hippocampal Nicotinic Receptors in Schizophrenia," *Biological Psychiatry*, vol. 38, pp. 22-33 (1995).

Freedman, Robert, et al., "The Genetics of Sensory Gating Deficits in Schizophrenia," *Current Psychiatry Reports*, vol. 5, pp. 155-161 (2003).

Gallowitsch-Puerta, Margot, et al., "Neuro-immune interactions via the cholinergic anti-inflammatory pathway," *Life Sciences*, vol. 80, No. 24-25, pp. 2325-2329 (May 30, 2007).

Giebelen, Ida A., et al., "Stimulation of α7 Cholinergic Receptors Inhibits Lipopolysaccharide-Induced Neutrophil Recruitment by a Tumor Necrosis Factor α-Independent Mechanism," *Shock*, vol. 27, No. 4, pp. 443-447 (2007).

Goldstein, Richard, et al., "Cholinergic Agonists Inhibit LPS Induced Whole Blood TNF Release Ex Vivo in Patients With Severe Sepsis: A Pilot Study," *Academic Emergency Medicine*, vol. 14, No. 5, Suppl. 1, pp. S185-S186 Abstract 474 (May 2007).

Harrington, C.R., et al., "Senile Dementia of Lewy Body Type and Alzheimer Type Are Biochemically Distinct in Terms of Paired Helical Filaments and Hyperphosphorylated Tau Protein," *Dementia*, vol. 5, pp. 215-228 (1994).

Hashimoto, Kenji, et al., "Phencyclidine-Induced Cognitive Deficits in Mice Are Improved by Subsequent Subchronic Administration of the Novel Selective α7 Nicotinic Receptor Agonist SSR180711," *Biological Psychiatry*, vol. 63, pp. 92-97 (2008).

Hauser, T.A., et al., "TC-5619: An alpha7 neuronal nicotinic receptor-selective agonist that demonstrates efficacy in animal models of the positive and negative symptoms and cognitive dysfunction of schizophrenia," *Biochemical Pharmacology*, vol. 78, No. 7, pp. 803-812 (Oct. 1, 2009).

(56) References Cited

OTHER PUBLICATIONS

Haydar, Simon N., et al., "SAR and biological evaluation of SEN12333/WAY-317538: Novel alpha 7 nicotinic acetylcholine receptor agonist," *Bioorganic & Medicinal Chemistry*, vol. 17, pp. 5247-5258 (2009).
Heeschen, Christopher, et al., "A novel angiogenic pathway mediated by non-neuronal nicotinic acetylcholine receptors," *The Journal of Clinical Investigation*, vol. 110, No. 4, pp. 527-536 (Aug. 2002).
Jeyarasasingam, G., et al., "Stimulation of Non-α7 Nicotinic Receptors Partially Protects Dopaminergic Neurons From 1-Methyl-4-Phenylpyridinium-Induced Toxicity in Culture," *Neuroscience*, vol. 109, No. 2, pp. 275-285 (2002).
Jin, Y., et al., "Genomic polymorphisms within alpha 7 nicotinic acetylcholine receptor and severe sepsis in Chinese Han population," *International Journal of Immunogenetics*, vol. 37, pp. 361-365 (2010).
Kuzmin, Alexander, et al., "Effects of subunit selective nAch receptors on operant ethanol self-administration and relapse-like ethanol-drinking behavior," *Psychopharmacology*, vol. 203, pp. 99-108 (2009).
Leiser, Steven C., et al., "A cog in cognition: How the α7 nicotinic acetylcholine receptor is geared towards improving cognitive defects," *Pharmacology & Therapeutics*, vol. 122, No. 3, pp. 302-311 (Jun. 2009).
Leonard, S., et al., "Smoking and mental illness," *Pharmacology, Biochemistry and Behavior*, vol. 70, pp. 561-570 (2001).
Liu, Chong, et al., "Antishock effect of anisodamine involves a novel pathway for activating α7 nicotinic acetylcholine receptor," *Critical Care Medicine*, vol. 37, No. 2, pp. 634-641 (2009).
Mansvelder, Huibert D., et al., "Nicotinic modulation of neuronal networks: from receptors to cognition," *Psychopharmacology*, vol. 184, pp. 292-305 (2006).
Marrero, Mario B., et al., "Convergence of alpha 7 nicotinic acetylcholine receptor-activated pathways for anti-apoptosis and anti-inflammation: Central role for JAK2 activation of STAT3 and NF-κB," *Brain Research*, vol. 1256, pp. 1-7 (2009).
Martin, Laura F., et al., "Sensory Gating and Alpha-7 Nicotinic Receptor Gene Allelic Variants in Schizoaffective Disorder, Bipolar Type," *American Journal of Medical Genetics Part B: Neuropsychiatric Genetics*, vol. 144B, No. 5, pp. 611-614 (Jul. 5, 2007).
Martin, Laura F., et al., "Alpha-7 nicotinic receptor agonists: potential new candidates for the treatment of schizophrenia," *Psychopharmacology*, vol. 174, pp. 54-64 (2004).
McKay, Bruce E., et al., "Regulation of synaptic transmission of plasticity by neuronal nicotinic acetylcholine receptors," *Biochemical Pharmacology*, vol. 74, pp. 1120-1133 (2007).
Miyaura, Norio, et al., "Palladium-Catalyzed Cross-Coupling Reactions of Organoboron Compounds," *Chemical Reviews*, vol. 95, pp. 2457-2483 (1995).
Nagele, R.G., et al., "Intracellular Accumulation of β-Amyloid$_{1-42}$ in Neurons is Facilitated by the α7 Nicotinic Acetylcholine Receptor in Alzheimer's Disease," *Neuroscience*, vol. 110, No. 2, pp. 199-211 (2002).
NG, Herman J., et al., "Nootropic α7 nicotinic receptor allosteric modulator derived from GABA$_A$ receptor modulators," *Proceedings of the National Academy of Sciences*, vol. 104, No. 19, pp. 8059-8064 (May 8, 2007).
Nizri, Eran, et al., "The Role of Cholinergic Balance Perturbation in Neurological Diseases," *Drug News & Perspectives*, vol. 20, No. 7, pp. 421-429 (Sep. 2007).
Nordberg, Agneta, et al., "Neuroprotection in Alzheimer's Disease—New Strategies for Treatment," *Neurotoxicity Research*, vol. 2, pp. 157-165 (2000).
O'Donnell, Christopher J., et al., "Discovery of 4-(5-Methyloxazolo[4,5-*b*]pyridine-2-yl)-1,4-diazabicyclo[3.2.2]nonane (CP-810,123), a Novel α7 Nicotinic Acetylcholine Receptor Agonist for the Treatment of Cognitive Disorders in Schizophrenia: Synthesis, SAR Development, and in Vivo Efficacy in Cognition Models," *Journal of Medicinal Chemistry*, vol. 53, pp. 1222-1237 (2010).
Olincy, Ann, et al., "Proof-of-Concept Trial of an α7 Nicotinic Agonist in Schizophrenia," *Archives of General Psychiatry*, vol. 63, pp, 630-638 (Jun. 2006).
Olincy, Ann, "Nicotine Receptor Dysfunction in Schizophrenia and Therapeutic Effects of Nicotine Agonist DMXBA," *Biological Psychiatry*, vol. 57, p. 13S, Abstract No. 44 (2005).
Paterson, David, et al., "Neuronal nicotinic receptors in the human brain," *Progress in Neurobiology*, vol. 61, pp. 75-111 (2000).
Peña, Geber, et al., "Unphosphorylated STAT3 modulates alpha7 nicotinic receptor signaling and cytokine production in sepsis," *European Journal of Immunology*, vol. 40, No. 9, pp. 2580-2589 (Sep. 2010).
Peng, ZZ, et al., "The transmission of disequilibrium analysis between neuronal nicotinic acetylcholine receptor alpha 7 subunit gene polymorphisms and schizophrenia," *Zhonghua Yi Xue Yi Chuan Xue Za Zhi*, vol. 25, No. 2, pp. 154-158 (Apr. 2008).
Perry, Elaine, et al., "Nicotinic receptor subtypes in human brain ageing, Alzheimer and Lewy body diseases," *European Journal of Pharmacology*, vol. 393, pp. 215-222 (2000).
Pfefferkorn, Jeffrey A., et al., "Development of a practical synthesis of novel, pyrrole-based HMG-CoA reductase inhibitors," *Tetrahedron*, vol. 63, pp. 8124-8134 (2007).
Pichat, Philippe, et al., "SSR180711, a Novel Selective α7 Nicotinic Receptor Partial Agonist: (II) Efficacy in Experimental Models Predictive of Activity Against Cognitive Symptoms of Schizophrenia," *Neuropsychopharmacology*, vol. 32, pp. 17-34 (2007).
Redrobe, John P., et al., "α7 nicotinic acetylcholine receptor activation ameliorates scopolamine-induced behavioural changes in a modified continuous Y-maze task in mice," *European Journal of Pharmacology*, vol. 602, pp. 58-65 (2009).
Remingtons' Pharmaceutical Sciences, 18$^{th}$ Edition, p. 1445 (1990).
Roncarati, Renza, et al., "Procognitive and Neuroprotective Activity of a Novel α7 Nicotinic Acetylcholine Receptor Agonist for Treatment of Neruodegenerative and Cognitive Diseases," *The Journal of Pharmacology and Experimental Therapeutics*, vol. 329, No. 2, pp. 459-468 (2009).
Rosas-Ballina, M., et al., "Cholinergic control of inflammation," *Journal of Internal Medicine*, vol. 265, pp. 663-679 (2009).
Rosas-Ballina, Mauricio, et al., "The Selective α7 Agonist GTS-21 Attenuates Cytokine Production in Human Whole Blood and Human Monocytes Activated by Ligands for TLR2, TLR3, TLR4, TLR9, and RAGE," *Molecular Medicine*, vol. 15, No. 7-8, pp. 195-202 (Jul.-Aug. 2009).
Rowbotham, Michael C., et al., "A randomized, double-blind, placebo-controlled trial evaluating the efficacy and safety of ABT-594 in patients with diabetic peripheral neuropathic pain," *Pain*, vol. 146, pp. 245-252 (2009).
Rowley, T.J., et al., "Antinociceptive and anti-inflammatory effects of choline in a mouse model of postoperative pain," *British Journal of Anaesthesia*, vol. 105, No. 2 pp. 201-207 (2010).
Rubboli, F., et al., "Distribution of Neuronal Nicotinic Receptor Subunits in Human Brain," *Neurochemistry International*, vol. 25, No. 1, pp. 69-71 (1994).
Sanberg, Paul R., et al., "Nicotine for the Treatment of Tourette's Syndrome," *Pharmacology & Therapeutics*, vol. 74, No. 1, pp. 21-25 (1997).
Schuller, Hildegard M., et al., "Interaction of tobacco-specific toxicants with the neuronal α$_7$ nicotinic acetylcholine receptor and its associated mitogenic signal transduction pathway: potential role in lung carcinogenesis and pediatric lung disorders," *European Journal of Pharmacology*, vol. 393, pp. 265-277 (2000).
Solinas, Marcello, et al., "Nicotinic α$_7$ Receptors as a New Target for Treatment of Cannabis Abuse," *The Journal of Neuroscience*, vol. 27, No. 21, pp. 5615-5620 (May 23, 2007).
Stahl, P. Heinrich, et al., *Handbook of Pharmaceutical Salts: Properties, Selection, and Use*, Wiley-VCH, Weinheim, pp. 1-374 (2002).
Suemaru, K, et al., "Involvement of neuronal nicotinic receptor in psychiatric disorders," *Nihon Yakurigaku Zasshi*, vol. 119, No. 5, pp. 295-300 (May 2002).

(56) References Cited

OTHER PUBLICATIONS

Thomsen, Morten S., et al., "Cognitive improvement by Activation of α7 Nicotinic Acetylcholine Receptors: From Animal Models to Human Pathophysiology," *Current Pharmaceutical Design*, vol. 16, pp. 323-343 (2010).

Timmermann, Daniel B., et al., "An Allosteric Modulator of the α7 Nicotinic Acetylcholine Receptor Possessing Cognition-Enhancing Properties in Vivo," *The Journal of Pharmacology and Experimental Therapeutics*, vol. 323, No. 1, pp. 294-307 (2007).

Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).

Tsuang, Debby W., et al., "Examination of Genetic Linkage of Chromosome 15 to Schizophrenia in a Large Veterans Affairs Cooperative Study Sample," *American Journal of Medical Genetics (Neuropsychiatric Genetics)*, vol. 105, pp. 662-668 (2001).

Van Kampen, Marja, et al., "AR-R 17779 improves social recognition in rats by activation of nicotinic α7 receptors," *Psychopharmacology*, vol. 172, pp. 375-383 (2004).

Verbois, S.L., et al. "Chronic nicotine treatment attenuates α7 nicotinic receptor deficits following traumatic brain injury," *Neuropharmacology*, vol. 44, pp. 224-233 (2003).

Wang, Hoau-Yan, et al., "Dissociating β-Amyloid from α7 Nicotinic Acetylcholine Receptor by a Novel Therapeutic Agent, S 24795, Normalizes α7 Nicotinic Acetylcholine and NMDA Receptor Function in Alzheimer's Disease Brain," *The Journal of Neuroscience*, vol. 29, No. 35, pp. 10961-10973 (Sep. 2, 2009).

Wang, Juan, et al., "Huperzine A Improves Chronic Inflammation and Cognitive Decline in Rats With Cerebral Hypoperfusion," *Journal of Neuroscience Research*, vol. 88, pp. 807-815 (2010).

Weiss, Robert B., et al., "A Candidate Gene Approach Identifies the CHRNA5-A3-B4 Region as a Risk Factor for Age-Dependent Nicotine Addition," *PLoS Genetics*, vol. 4, No. 7, e1000125, pp. 1-11 (Jul. 2008).

Westman, M., et al., "Cell Specific Synovial Expression of Nicotinic Alpha 7 Acetylcholine Receptor in Rheumatoid Arthritis and Psoriatic Arthritis," *Scandinavian Journal of Immunology*, vol. 70, pp. 136-140 (2009).

Wilens, Timothy E., et al., "Neuronal Nicotinic Receptor Agonists for the Treatment of Attention-Deficit/Hyperactivity Disorder: Focus on Cognition," *Biochemical Pharmacology*, vol. 74, No. 8, pp. 1212-1223 (Oct. 15, 2007).

Yadav, J. S., et al., "Zinc-mediated acylation and sulfonation of pyrrole and its derivatives," *Tetrahedron Letters*, vol. 43, pp. 8133-8135 (2002).

Young, Jared W., et al., "Impaired attention is central to the cognitive deficits observed in alpha 7 deficient mice," *European Neuropsychopharmacology*, vol. 17, pp. 145-155 (2007).

Young, Jared W., et al., "Nicotine Improves Sustained Attention in Mice: Evidence for Involvement of the α7 Nicotinic Acetylcholine Receptor," *Neurepsychopharmacology*, vol. 29, pp. 891-900 (2004).

Zhao, Xilong, et al., "Post-Stroke Dementia: Nootropic Drug Modulation of Neuronal Nicotinic Acetylcholine Receptors," *Annals New York Academy of Sciences*, vol. 939, pp. 179-186 (2001).

U.S. Appl. No. 14/655,878, filed Jun. 26, 2015.

U.S. Appl. No. 14/894,803, filed Nov. 30, 2015.

\* cited by examiner

PYRROLE DERIVATIVES AS ALPHA 7 NACHR MODULATORS

CROSS-REFERENCE TO RELATED APPLICATIONS

This patent application is a U.S. National Phase Patent Application of copending Internaional Patent Application No. PCT/IB2014/059674, filed Mar. 12, 2014, which claims the benefit of Indian Patent Application No. 754/MUM/2013, filed Mar. 13, 2013.

FIELD OF THE INVENTION

The present invention relates to pyrrole derivatives, their tautomeric forms, their stereoisomers, and their pharmaceutically acceptable salts, pharmaceutical compositions comprising one or more such compounds, and their use as nicotinic acetylcholine receptor α7 subunit (α7 nAChR) modulators.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in all of the autonomic ganglia, neuromuscular junctions, and the central nervous system. Two distinct classes of ACh target receptors viz. muscarinic (mAChRs) and the nicotinic (nAChRs) have been identified in the brain, forming a significant component of receptors carrying out its mnemonic and other vital physiological functions.

Neural nicotinic ACh receptors (NNRs) belong to the class of ligand-gated ion channels (LGIC) comprising five subunits (α2-α10, β2-β4) arranged in heteropentameric (α4β2) or homopentameric (α7) configuration (David Paterson et al., Progress in Neurobiology, 61(2000), 75-111). α4β2 and α7 nAChR constitute the predominant subtypes expressed in the mammalian brain. α7 nAChR has attained prominence as a therapeutic target due to its abundant expression in the learning and memory centers of brain, hippocampus and the cerebral cortex (F. Rubboli et al., Neurochem. Int., 1994, 25(1), 69-71). Particularly, α7 nAChR is characterized by a high $Ca^{2+}$ ion permeability, which is responsible for neurotransmitter release and consequent modulation of excitatory and inhibitory neurotransmission (Manickavasagom Alkondon et al., European Journal of Pharmacology, 393(2000), 59-67; Federico Dajas-Bailador et al., TRENDS in Pharmacological Sciences, 2004, 25(6), 317-324). Furthermore, high $Ca^{2+}$ ion influx also has implications on the long-term potentiation of memory via alterations in gene expression (Robert S. Bitner et al., The Journal of Neuroscience, 2007, 27(39), 10578-10587; Bruce E. McKay et al., Biochemical Pharmacology, 74(2007), 1120-1133).

Several recent studies have confirmed the role of α7 nAChR in neural processes like attention, memory and cognition (Hulbert D. Mansvelder et al., Psychopharmacology, (2006), 184, 292-305; Wai Kit Chan et al., Neuropharmacology, 52 (2007), 1641-1649; Jared W. Young et al., European Neuropsychopharmacology, (2007), 17, 145-155). Gene polymorphisms associated with the α7 nAChR protein CHRNA7 have been implicated in the genetic transmission of schizophrenia, related neurophysiological sensory gating deficits and resultant cognitive impairment (Robert Freedman et al., Biol. Psychiatry, 1995, 38, 22-33; Debby W. Tsuang et al., American Journal of Medical Genetics (Neuropsychiatric Genetics, 105, 662-668 (2001)). Also, preclinical studies in α7 nAChR knock-out and anti-sense oligonucleotide treated mice have demonstrated impaired attention and defective cognition underscoring the prominent role of α7 nAChR in cognition (Peter Curzon et al., Neuroscience Letters, 410 (2006), 15-19; Jared W. Young et al., Neuropsychopharmacology, (2004), 29, 891-900). Additionally, pharmacological blockade of α7 nAChR impairs memory and its activation enhances the same in preclinical rodent models, thereby implicating α7 nAChR as a target for cognitive enhancement (Kenji Hashimoto et al., Biol. Psychiatry, 2008, 63, 92-97).

Pathological brain function in sensory-deficit disorders has been associated with nicotinic cholinergic transmission particularly through α7 receptors (Robert Freedman et al., Biol. Psychiatry, 1995, 38, 22-33; T Debby W. Tsuang et al., American Journal of Medical Genetics (Neuropsychiatric Genetics), 105, 662-668 (2001); Robyn Carson et al., Neuromol., Med. (2008), 10, 377-384; S. Leonard et al., Pharmacology Biochemistry and Behavior, 70 (2001), 561-570; Robert Freedman et al., Current Psychiatry Report, 2003, 5, 155-161; Tyrone D. Cannon et. al., Current Opinion Psychiatry, 2005, 18, 135-140). A defective pre-attention processing of sensory information is understood to be the basis of cognitive fragmentation in schizophrenia and related neuropsychiatric disorders (Steven C. Leiser et al., Pharmacology&Therapeutics, 122 (3), (2009), 302-311). Genetic linkage studies have traced sharing of the α7 gene locus for several affective, attention, anxiety and psychotic disorders (S. Leonard et al., Pharmacology, Biochemistry and Behavior, 70 (2001), 561-570; Suemaru K. Folia et al., Folia Pharmacol. Jpn., 119, 295-300 (2002)).

Perturbations in the cholinergic and glutamatergic homeostasis have long been implicated as causative factors for a host of neurological diseases, including dementia(s) (Eran Nizri et al., Drug News Perspect., 2007, 20 (7), 421-429). Dementia is a severe, progressive, multi-factorial cognitive disorder affecting memory, attention, language, and problem solving. Nicotinic ACh receptor, particularly the interaction of α7 receptor with $\alpha\beta_{1-42}$, is implicated as an up-stream pathogenic event in Alzheimer's disease, which is a major causative factor for dementia (Hoau-Yan Wang et al., The Journal of Neuroscience, 2009, 29 (35), 10961-10973). Moreover, gene polymorphisms in CHRNA7 have been implicated in dementia with Lewy bodies (DLB) and Pick's disease (Agnes Feher et al., Dement. Geriatr. Cogn. Disord., 2009, 28, 56-62).

Disease modification potential of the nAChRs, particularly the α7 receptor, hasbeen recognized. For example, disease-modification of Alzheimer's disease (AD) and Parkinson's disease (PD) has been proposed by enhancing neuron survival and preventing neurodegeneration (Hoau-Yan Wang et al., The Journal of Neuroscience, 2009, 29 (35), 10961-10973; R. G. Nagele et al., Neuroscience, 2002, 110 (2), 199-211; G. Jeyarasasingam et al., Neuroscience, 2002, 109, 275-285). Additionally, it has been proposed that α7 nAChR induced activation of anti-apoptotic (BCL-2) and anti-inflammatory pathways in the brain could have neuroprotective effects in neurodegenerative diseases (Mario B. Marrero et al., Brain Research, 2009, 1256, 1-7). Dopamine-containing neurons of the ventral tegmental area (VTA) and laterodorsal tegmental nucleus (LDT) are known to express nicotinic ACh receptors, particularly the α4, α3, β2, β3, and β4 subunits (Alexander Kuzmin et al., Psychopharmacology, (2009), 203, 99-108). Nicotinic ACh receptors α4β2 and α3β4 have been identified by the candidate-gene approach to have a strong mechanistic link for nicotine addiction (Robert B. Weiss et al., PLoS Genetics, 2008, 4 (7), e1000125). α7 nAChR has particularly been studied for a putative role in cannabis addiction (Marcello Solinas et al., The Journal of Neuroscience, 2007, 27 (21), 5615-5620). Varenicline, a partial agonist of α4β2, has demonstrated better efficacy in reducing smoking addiction and relapse prevention than buproprion (Jon O. Ebbert et al., Patient Preference and Adherence, 2010, 4, 355-362).

The presence of a high-affinity nicotine binding site at α4β2 nAChR in the descending inhibitory pathways from the brainstem has sparked interest in the antinociceptive properties of nicotinic ACh receptor agonists like epibatidine (Michael Decker et al., Expert Opin. Investig. Drugs, (2001), 10 (10), 1819-1830). Several new developments have opened the area for the use of nicotinic modulators in pain therapy (Michael C. Rowbotham et al., PAIN, 146, (2009), 245-252).

Another key role of the α7 nAChR is its ability to modulate the production of pro-inflammatory cytokines, like interleukins (IL), tumor necrosis factor alpha (TNF-α), and high mobility group box (HMGB-1) in the central nervous system. Consequently, anti-inflammatory and antinociceptive effects have been demonstrated in pain disorders (M. Imad Damaj et al., Neuropharmacology, 39 (2000), 2785-2791). Additionally, 'cholinergic anti-inflammatory pathway' has been proposed to be a regulator of local and systemic inflammation and neuro-immune interactions through neural and humoral pathways (Margot Gallowitsch-Puerta et al., Life Sci., 2007, 80 (24-25), 2325-2329; Mauricio Rosas-Ballina et al., Mol. Med., 15 (7-8), 195-202 (2009); M. Rosas-Ballina et al., J. Intern. Med., 2009, 265, 663-679). Selective modulators of nicotinic ACh receptors, particularly the α7 type, like GTS-21, attenuate cytokine production and IL-1β after endotoxin exposure. Furthermore, α7 nAChR are understood to have a central role in arthritis pathogenesis and potential therapeutic strategy for treatment of joint inflammation (M. Westman et al., Scandinavian Journal of Immunology, 2009, 70, 136-140). A putative role for α7 nAChR has also been implicated in severe sepsis, endotoxemic shock and systemic inflammation (Y. Jin, et al., International Journal of Immunogenetics, 37, 361-365; Chong Liu et al., Crit. CareMed., 2009, 37 (2), 634-641).

Angiogenesis is a critical physiological process for cell survival and is pathologically important for cancer proliferation; several non-neural nicotinic ACh receptors, particularly α7, α5, α3, β2, and β4, are involved in such processes (Hugo R. Arias et al., International Journal of Biochemistryand Cell Biology, 41 (2009), 1441-1451; Christopher Heeschen et al., The Journal of Clinical Investigation, 2002, 110 (4), 527-536). The role of nicotinic ACh receptors in the development of cervical cancer, lung carcinogenesis and pediatric lung disorders in smoking-exposed population has been studied (Itzel E. Calleja-Macias et al., Int. J. Cancer., 124, 1090-1096 (2009); Hildegard M. Schuller et al., European Journal of Pharmacology, 393 (2000), 265-277). Several α7 nAChR agonists and partial agonists have been characterized for their efficacy in clinical and preclinical studies. EVP-6124, an agonist at α7 nAChR, has reportedly demonstrated a significant improvement in sensory processing and cognition biomarkers in Phase Ib study with patients suffering from schizophrenia (EnVivo Pharmaceuticals press release 2009, Jan. 12). GTS-21 (DMXB-Anabaseine), an α7 nAChR agonist, in the P II clinical trials, has reportedly shown efficacy in improving cognitive deficits in schizophrenia and the inhibition of endotoxin-induced TNF-α release (Ann Olincy et al., Biol. Psychiatry, 2005, 57(8, Suppl.), Abst 44; Ann Olincy et al., Arch. Gen. Psychiatry, 2006, 63, 630-638; Richard Goldstein et al., Acad. Emerg. Med., 2007, 14 (5), s185-s186). CP-810123, anal nAChR agonist, reportedly exhibits protection against scopolamine-induced dementia and inhibition of amphetamine-induced auditory evoked potentials in preclinical studies (Christopher J. O'Donnell et al., J. Med. Chem., 2010, 53, 1222-1237). SSR-180711A, also an α7 nAChR agonist, reportedly enhances learning and memory, and protects against MK-801/scopolamine-induced memory loss and prepulse inhibition in preclinical studies (John P. Redrobe et al., European Journal of Pharmacology, 602 (2009), 58-65; John Dunlop et al., Journal of Pharmacology and Experimental Therapeutics, 2009, 328, 766-776; Philippe Pichat et al., Neuropsychopharmacology, 2007, 32, 17-34). SEN-12333 reportedly protects against scopolamine-induced amnesia in a passive avoidance test in preclinical studies (Renza Roncarati et al., The Journal of Pharmacology and Experimental Therapeutics, 2009, 329, 459-468). AR-R-17779, an agonist of the α7 nAChR, reportedly exhibits an improvement in the social recognition task performed in rats (Marja Van Kampen et al., Psychopharmacology, 2004, 172, 375-383). ABBF, an agonist of the α7 nAChR, reportedly improves social recognition memory and working memory in the Morris maze task in rats (Frank G. Boess et al., The Journal of Pharmacology and Experimental Therapeutics, 2007, 321, 716-725). TC-5619, a selective α7 nAChR agonist has reportedly demonstrated efficacy in animal models of positive and negative symptoms and cognitive dysfunction in schizophrenia (T. A. Hauser et al., Biochemical Pharmacology, 78 (2009), 803-812).

An alternative strategy to reinforce or potentiate the endogenous cholinergic neurotransmission of ACh without directly stimulating the target receptor is the positive allosteric modulation (PAM) of α7 nAChR (E. X. Albuquerque et al., Alzheimer Diseasesand Associated Disorder, Vol. 15, Suppl 1, S19-S25). Several PAMs have been characterized, albeit only in preclinical stages of discovery. A-86774, an α7 nAChR PAM, reportedly improves sensory gating in DBA/2 mice by significantly reducing the T: C ratio in a preclinical model of schizophrenia (Ramin Faghih et al., Journal of Medicinal Chemistry, 2009, 52, 3377-3384). XY-4083, an α7 nAChR PAM, reportedly normalizes the sensorimotor gating deficits in the DBA/2 mice and memory acquisition in the 8-arm radial maze test without altering the receptor desensitization kinetics (Herman J. Hg et al., PNAS, 2007, 104 (19), 8059-8064). Yet another PAM, PNU-120596, reportedly alters α7 nAChR desensitization kinetics and simultaneously protecting against the disruption of prepulse inhibition by MK-801. NS-1738, another PAM, reportedly exhibits efficacy in-vivo in the animal models of social recognition and spatial memory acquisition in the Morris maze task (Daniel B. Timmermann et al., Journal of Pharmacology and Experimental Therapeutics, 2007, 323, 294-307). In addition, several patents/applications published are listed below—US 2006/0142349, US 2007/0142450, US 2009/0253691, WO 2007/031440, WO 2009/115547, WO 2009/135944, WO 2009/127678, WO 2009/127679, WO 2009/043780, WO 2009/043784, U.S. Pat. Nos. 7,683,084, 7,741,364, WO 2009/145996, US 2010/0240707, WO 2011/064288, US 2010/0222398, US 2010/0227869, EP 1866314, WO 2010/130768, WO 2011/036167, US 2010/0190819, WO 2012/104782, WO 2012/114285, WO 2012/131576, WO 2013/005153, and WO 2013/132380, which reportedly disclose efficacy of allosteric modulators of nicotinic ACh receptors, underscoring their therapeutic potential.

Despite the foregoing proposals in the art, there exists a need for novel modulators of the nicotinic acetylcholine receptors, particularly the α7 nAChR, pharmaceutical compositions comprising such modulators, and methods of treating diseases, disorders, or conditions that are treatable or preventable by the use of such modulators.

BRIEF SUMMARY OF THE INVENTION

The present invention providesa compound of the general formula (I), its tautomeric forms, its stereoisomers, its pharmaceutically acceptable salts, its combinations with suitable medicament, its pharmaceutical compositions and its use as nicotinic acetylcholine receptor α7 subunit (α7 nAChR) modulator.

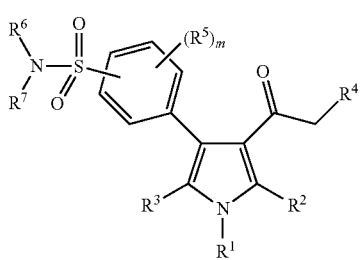

According to one aspect of the present invention, there is provided a compound represented by the general formula (I), its tautomeric forms, its stereoisomers, its pharmaceutically acceptable salts, its combinations with suitable medicament and its pharmaceutical compositions, wherein $R^1$ to $R^7$ and m are described in details below.

Thus the present invention further provides a pharmaceutical composition, containing the compound of the general formula (I) as defined herein, its tautomeric forms, its stereoisomers, and its pharmaceutically acceptable salts in combination with the usual pharmaceutically employed carriers, diluents, and the like are useful for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition containing a compound of the general formula (I) as defined herein, its tautomeric forms, its stereoisomers, its pharmaceutically acceptable salts, its polymorphs, its solvates, and/or its optical isomers in combination with pharmaceutically acceptable carriers, diluents, and the like, which is useful for the treatment and/or prophylaxis of diseases, disorders, or conditions classified or diagnosed as major or minor neurocognitive disorders, or disorders arising due to neurodegeneration.

The present invention also provides a method of treatment wherein a compound of formula (I), as defined herein, is administered in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, or traumatic brain injury.

The present invention also provides method of treatment wherein a compound of formula (I), as defined herein, is administered in combination with or as an adjunct to acetylcholinesterase inhibitors, disease modifying drugs or biologics for neurodegenerative disorders, dopaminergic drugs, antidepressants, or a typical or atypical antipsychotic.

The present invention also provides the use of a compound of formula (I) as defined herein in the preparation of a medicament for treating a disease, disorder, or condition selected from the group of disorders classified or diagnosed as major or minor neurocognitive disorders and disorders arising due to neurodegeneration.

The present invention also provides the use of a compound of formula (I) as defined herein in the preparation of a medicament for treating a disease, disorder, or condition selected from attention deficit hyperactivity disorders, schizophrenia, cognitive disorders, Alzheimer's disease, Parkinson's dementia, vascular dementia or dementia associated with Lewy bodies, and traumatic brain injury.

The present invention also provides the use of compound of formula (I) as defined herein in combination with or as an adjunct to acetylcholinesterase inhibitors, disease modifying drugs or biologics for neurodegenerative disorders, dopaminergic drugs, antidepressants, or a typical or atypical antipsychotic.

DETAILED DESCRIPTION OF THE INVENTION

The present invention provides a compound of the general formula (I), its tautomeric forms, its stereoisomers, its pharmaceutically acceptable salts, its combinations with suitable medicament, and its pharmaceutical compositions,

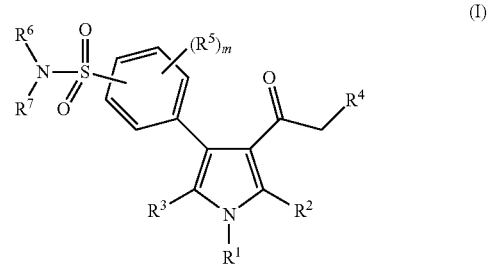

wherein,
- R¹ is selected from substituted- or unsubstituted-cycloalkyl, and substituted- or unsubstituted-aryl, substituted- or unsubstituted-heteroaryl and substituted- or unsubstituted-heterocyclyl;
- R² is selected from substituted- or unsubstituted-alkyl, perhaloalkyl, substituted- or unsubstituted-cycloalkyl, and substituted- or unsubstituted-heterocyclyl;
- R³ is selected from substituted- or unsubstituted-alkyl, perhaloalkyl, substituted- or unsubstituted-cycloalkyl, and substituted- or unsubstituted-heterocyclyl;
- R⁴ is selected from substituted- or unsubstituted-cycloalkyl, and substituted- or unsubstituted-heterocyclyl;
- R⁵ is independently selected at each occurrence from halogen, substituted- or unsubstituted-alkyl, perhaloalkyl, substituted- or unsubstituted-cycloalkyl, —OR$^{7b}$, —NR⁶R⁷, and —C(=O)R$^{7a}$; or
- two R⁵ groups and the carbon atoms to which they are attached together from 5 to 6 membered carbocycle or 5 to 6 membered heterocycle, the carbocycle or heterocycle is optionally substituted with 1 to 3 substituent(s) independently selected from oxo, halogen, cyano, and alkyl;
- R⁶ and R⁷ are independently selected from hydrogen, substituted- or unsubstituted-alkyl, substituted- or unsubstituted-cycloalkyl, and —C(=O)R$^{7a}$;
- R$^{7a}$ is selected from substituted- or unsubstituted-alkyl, perhaloalkyl, and substituted- or unsubstituted-cycloalkyl;
- R$^{7b}$ is selected from hydrogen, substituted- or unsubstituted-alkyl, perhaloalkyl, and substituted- or unsubstituted-cycloalkyl;
- m is an integer selected from 0, 1 and 2;

wherein,
- when the alkyl group is substituted, it is substituted with 1 to 3 substituents independently selected from halogen, perhaloalkyl, cycloalkyl, —OR$^{8b}$, —N(H)R⁸, and —N(alkyl)R⁸;
- when the cycloalkyl and the carbocycle groups are substituted, each of them is substituted with 1 to 3 substituents independently selected from halogen, alkyl, perhaloalkyl, —OR$^{8b}$, —N(H)R⁸, and —N(alkyl)R⁸;
- when the aryl group is substituted, it is substituted with 1 to 3 substituents independently selected from halogen, nitro, cyano, hydroxy, alkyl, perhaloalkyl, cycloalkyl, heterocyclyl, —O-alkyl, —O-perhaloalkyl, —N(alkyl)alkyl, —N(H)alkyl, —NH₂, —SO₂-alkyl, —SO₂-perhaloalkyl, —N(alkyl)C(=O)alkyl, —N(H)C(=O)alkyl, —C(=O)N(alkyl)alkyl, —C(=O)N(H)alkyl, —C(=O)NH₂, —SO₂N(alkyl)alkyl, —SO₂N(H)alkyl, and —SO₂NH₂;
- when the heteroaryl group is substituted, it is substituted with 1 to 3 substituents independently selected from halogen, nitro, cyano, hydroxy, alkyl, perhaloalkyl, —O-alkyl, —O-perhaloalkyl, —N(alkyl)alkyl, —N(H)alkyl, and —NH₂;
- when the heterocyclyl group is substituted, it can be substituted either on a ring carbon atom(s) or on a ring hetero atom; when it is substituted on a ring carbon atom(s), it is substituted with 1 to 3 substituents independently selected from halogen, oxo, alkyl, perhaloalkyl, and OR$^{8b}$; and when the 'heterocyclyl' group is substituted on a ring nitrogen, it is substituted with a substituent selected from alkyl, cycloalkyl, —SO₂alkyl, and —C(=O)R$^{8a}$;
- R⁸ is selected from hydrogen, alkyl, and cycloalkyl;
- R$^{8a}$ is selected from alkyl, perhaloalkyl, and cycloalkyl;
- R$^{8b}$ is selected from hydrogen, alkyl, perhaloalkyl, and cycloalkyl.

In accordance with an embodiment of the invention, R¹ is selected from substituted- or unsubstituted-cycloalkyl, substituted- or unsubstituted-phenyl, substituted- or unsubstituted-pyridyl, and substituted- or unsubstituted-piperidinyl.

In certain embodiments, R¹ is selected from 4-flurophenyl, 4-chlorophenyl, 4-(dimethylamino)phenyl, 4-chloro-3-methylphenyl, cyclohexyl, 3-pyridyl, and N-methylpiperidinyl.

In any of the above embodiments, R² is a substituted- or unsubstituted-alkyl.

In certain embodiments, R² is selected from methyl and ethyl.

In any of the above embodiments, R³ is selected from substituted- or unsubstituted-alkyl, perhaloalkyl, and substituted- or unsubstituted-cycloalkyl.

In certain embodiments, R³ is selected from methyl, trifluoromethyl, and cyclopropyl.

In any of the above embodiments, R⁴ is selected from substituted- or unsubstituted-cycloalkyl, and substituted- or unsubstituted-pyrrolidinyl.

In certain embodiments, R⁴ is selected from cyclopropyl, cyclobutyl, cyclopentyl, pyrrolidinyl, and 2-oxopyrrolidinyl.

In any of the above embodiments, m is selected from 0 and 1.

In any of the above embodiments, R⁵ is halogen.

In any of the above embodiments, R⁶ and R⁷ are hydrogen.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

General terms used in formula can be defined as follows; however, the meaning stated should not be interpreted as limiting the scope of the term per se.

The term "alkyl", as used herein, means a straight or branched hydrocarbyl chain containing from 1 to 20 carbon atoms. Preferably, the alkyl group contains 1 to 10 carbon atoms. More preferably, alkyl group contains up to 6 carbon atoms. Examples of alkyl groups include, but are not limited to, methyl, ethyl, n-propyl, isopropyl, n-butyl, sec-butyl, iso-butyl, tert-butyl, n-pentyl, isopentyl, neopentyl, and n-hexyl.

In a substituted alkyl group, the alkyl group is substituted with 1 to 3 substituents independently selected from halogen, perhaloalkyl, cycloalkyl, —OR$^{8b}$, —N(H)R$^8$, —N(alkyl)R$^8$; wherein R$^8$ is selected from hydrogen, alkyl, and cycloalkyl; R$^{8b}$ is selected from hydrogen, alkyl, perhaloalkyl, and cycloalkyl.

The term "perhaloalkyl" used herein means an alkyl group as defined hereinabove wherein all of the hydrogen atoms of said alkyl group are substituted with halogen. The perhaloalkyl group is exemplified by trifluoromethyl, pentafluoroethyl, and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[410]heptane, bicyclo[3.2.0]heptanes, octahydro-1H-indene, spiro[2.5]octane, spiro[4.5]decane, spiro[bicyclo[4.1.0]heptane-2,1'-cyclopentane], hexahydro-2'H-spiro[cyclopropane-1,1'-pentalene]. Tricyclic ring systems are the systems wherein the bicyclic systems as described about are further annulated with third ring, which may be alicyclic ring or aromatic ring. Tricyclic ring systems are also exemplified by a bicyclic ring system in which two non-adjacent carbon atoms of the bicyclic ring are linked by a bond or an alkylene bridge. Examples of tricyclic-ring systems include, but are not limited to, tricyclo[3.3.1.0$^{3.7}$]nonane and tricyclo[3.3.1.1$^{3.7}$]decane (adamantane).

The term "carbocycle" as used herein, means a cyclic system made up of carbon atoms, which includes cycloalkyl and aryl.

When the cycloalkyl or the carbocycle groups are substituted, they are substituted with 1 to 3 substituents independently selected from halogen, alkyl, perhaloalkyl, —OR$^{8b}$, —N(H)R$^8$, and —N(alkyl)R$^8$; wherein R$^8$ is selected from hydrogen, alkyl, and cycloalkyl; R$^{8b}$ is selected from alkyl, perhaloalkyl, and cycloalkyl.

The term "aryl" refers to a monocyclic, bicyclic or tricyclic aromatic hydrocarbon ring system. Examples of aryl groups include phenyl, naphthyl, anthracenyl, fluorenyl, indenyl, azulenyl, and the like. Aryl group also includes partially saturated bicyclic and tricyclic aromatic hydrocarbons such as tetrahydro-naphthalene.

When the aryl group is substituted, it is substituted with 1 to 3 substituents independently selected from halogen, nitro, cyano, hydroxy, alkyl, perhaloalkyl, cycloalkyl, heterocyclyl, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, and —SO$_2$NH$_2$.

The term "heteroaryl" refers to a 5-14 membered monocyclic, bicyclic, or tricyclic ring system having 1 to 4 ring heteroatoms selected from O, N, and S, and the remainder ring atoms being carbon (with appropriate hydrogen atoms unless otherwise indicated), wherein at least one ring in the ring system is aromatic. Heteroaryl groups are optionally substituted with one or more substituents. In one embodiment, 0, 1, 2, 3, or 4 atoms of each ring of a heteroaryl group is substituted by a substituent. Examples of heteroaryl groups include, but not limited to, pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1,3]dioxol-4-yl, benzo[1,3]dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl and the like.

When the heteroaryl group is substituted, it is substituted with 1 to 3 substituents independently selected from halogen, nitro, cyano, hydroxy, alkyl, perhaloalkyl, —O-alkyl, —O-perhaloalkyl, —N(alkyl)alkyl, —N(H)alkyl, and —NH$_2$.

The term "heterocyclyl" as used herein, means a 'cycloalkyl' group wherein one or more of the carbon atoms are replaced by —O—, —S—, —S(O$_2$)—, —S(O)—, —N(R$^m$)—, —Si(R$^m$)R$^n$—, wherein, R$^m$ and R$^n$ are independently selected from hydrogen, alkyl, aryl, heteroaryl, cycloalkyl, and heterocyclyl. The heterocycle may be connected to the parent molecular moiety through any carbon atom or any nitrogen atom contained within the heterocycle. Examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl (thiomorpholine sulfone), thiopyranyl, and trithianyl. Examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclyl systems such as azabicyclo[3.2.1]octane, azabicyclo[3.3.1]nonane and the like.

The heterocyclyl group, when it is substituted, it is substituted on ring carbon atom(s) and/or ring nitrogen atom. For example, it is substituted on a ring carbon atom(s) with 1 to 3 substituents independently selected from halogen, oxo, alkyl, perhaloalkyl, and —OR$^{8b}$; wherein R$^{8b}$ is selected from hydrogen, alkyl, perhaloalkyl, and cycloalkyl.

When the heterocyclyl group is substituted on ring nitrogen, it is substituted with a substituent selected from alkyl, cycloalkyl, —SO$_2$alkyl and —C(=O)R$^{8a}$; wherein R$^{8a}$ is selected from alkyl, perhaloalkyl, and cycloalkyl.

When a parent group is substituted with an "oxo" group, it means a divalent oxygen (=O) becomes attached to a carbon atom of the parent group. For example, when a $CH_2$ group is substituted with an oxo substituent, the parent $CH_2$ group becomes a carbonyl (C=O) group; thus, oxo substituted on cyclohexane forms a cyclohexanone, for example.

The term "annulated" means the ring system under consideration is either annulated with another ring at a carbon atom of the cyclic system or across a bond of the cyclic system as in the case of fused or spiro ring systems.

The term "bridged" means the ring system under consideration contain an alkylene bridge having 1 to 4 methylene units joining two non-adjacent ring atoms.

A compound, its stereoisomers, racemates, and pharmaceutically acceptable salt thereof as described hereinabove, wherein, the compound of general formula (I) is selected from:

1. 4-(1-(4-chlorophenyl)-4-(2-cyclopropylacetyl)-2,5-dimethyl-1H-pyrrol-3-yl)benzenesulfonamide (compound 1);
2. 4-(1-(4-chlorophenyl)-2,5-dimethyl-4-(2-(2-oxopyrrolidin-1-yl)acetyl)-1H-pyrrol-3-yl)benzenesulfonamide (compound 2);
3. 4-(1-(4-chlorophenyl)-2,5-dimethyl-4-(2-(pyrrolidin-1-yl)acetyl)-1H-pyrrol-3-yl)benzenesulfonamide (compound 3);
4. 4-(4-(2-cyclopropylacetyl)-1-(4-(dimethylamino)phenyl)-2,5-dimethyl-1H-pyrrol-3-yl)benzenesulfonamide (compound 4);
5. 4-(4-(2-cyclopropylacetyl)-1-(4-fluorophenyl)-2,5-dimethyl-1H-pyrrol-3-yl)benzenesulfonamide (compound 5);
6. 4-(1-(4-chlorophenyl)-4-(2-cyclobutylacetyl)-2,5-dimethyl-1H-pyrrol-3-yl)-2-fluorobenzenesulfonamide (compound 6);
7. 4-(1-(4-chloro-3-methylphenyl)-4-(2-cyclopropylacetyl)-2,5-dimethyl-1H-pyrrol-3-yl)benzenesulfonamide (compound 7);
8. 4-(1-(4-chlorophenyl)-4-(2-cyclopropylacetyl)-2,5-dimethyl-1H-pyrrol-3-yl)-2-fluorobenzenesulfonamide (compound 8);
9. 4-(1-(4-chlorophenyl)-4-(2-cyclobutylacetyl)-2,5-dimethyl-1H-pyrrol-3-yl)benzenesulfonamide (compound 9);
10. 4-(1-(4-chlorophenyl)-2-cyclopropyl-4-(2-cyclopropylacetyl)-5-methyl-1H-pyrrol-3-yl)benzenesulfonamide (compound 10);
11. 4-(1-(4-chloro-3-methylphenyl)-4-(2-cyclopropylacetyl)-2,5-dimethyl-1H-pyrrol-3-yl)-2-fluorobenzenesulfonamide (compound 11);
12. 4-(1-(4-chlorophenyl)-4-(2-cyclopentylacetyl)-2,5-dimethyl-1H-pyrrol-3-yl)benzenesulfonamide (compound 12);
13. 4-(1-(4-chlorophenyl)-4-(2-cyclopentylacetyl)-2,5-dimethyl-1H-pyrrol-3-yl)-2-fluorobenzenesulfonamide (compound 13);
14. 4-(1-(4-chlorophenyl)-4-(2-cyclopropylacetyl)-5-ethyl-2-methyl-1H-pyrrol-3-yl)benzenesulfonamide (compound 14);
15. 4-(1-(4-chlorophenyl)-4-(2-cyclopropylacetyl)-5-methyl-2-(trifluoromethyl)-1H-pyrrol-3-yl)benzenesulfonamide (compound 15);
16. 4-(1-cyclohexyl-4-(2-cyclopropylacetyl)-2,5-dimethyl-1H-pyrrol-3-yl)benzenesulfonamide (compound 16);
17. 4-(4-(2-cyclopropylacetyl)-2,5-dimethyl-1-(pyridin-3-yl)-1H-pyrrol-3-yl)benzenesulfonamide (Compound 17); and
18. 4-(4-(2-cyclopropylacetyl)-2,5-dimethyl-1-(1-methylpiperidin-4-yl)-1H-pyrrol-3-yl)benzenesulfonamide (Compound 18).

According to another aspect of the present invention, the compound of general formula (I) where all the symbols are as defined earlier was prepared by methods described below. However, the synthetic methods should not be construed limiting the invention, which lies in the whole genus described by compound of formula (I) above.

According to another aspect of the present invention, the compounds of general formula (I) where all the symbols are as defined earlier are prepared by methods described below. However, the synthetic methods should not be construed as limiting the invention, which lies in the whole genus described by the compound of formula (I) above.

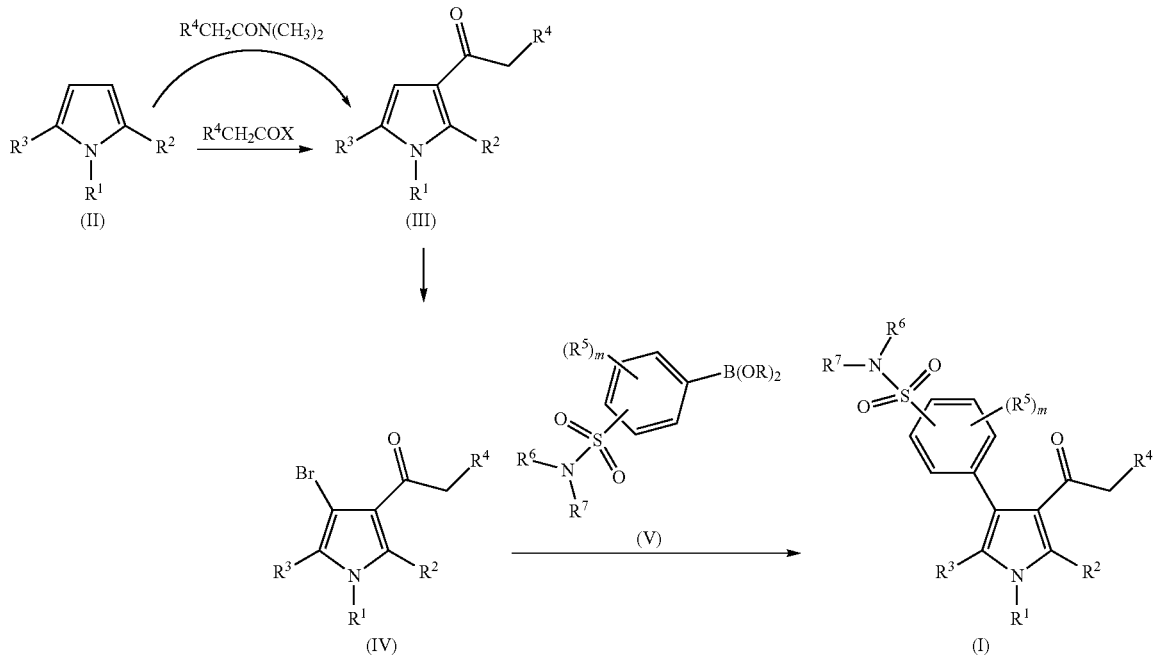

Scheme - I

Scheme 1 shows a method for the synthesis of the compound of the formula (I) (where $R^1$, $R^2$, $R^3$, $R^4$, $R^5$, $R^6$, $R^7$ and m are as described under compound of generic formula (I)), from compound represented by general formula (II) (where $R^1$, $R^2$ and $R^3$ are same as defined earlier). The compound of formula (II) can be prepared according to the procedure described in literature (Jiuxi Chen et al., Synthetic Communications, 2009, 39(23), 4180-4198).

The compound of formula (II) is reacted with $R^4CH_2COX$ (acid halides) (where $R^4$ is as defined earlier) in the presence of an acid or zinc under Friedel-Crafts reaction conditions as described in the literature (J. S. Yadav et al., Tetrahedron Letters, 2002, 43, 8133-8135) to obtain the compounds of the formula (III) (where $R^1$, $R^2$, $R^3$ and $R^4$ are same as defined earlier). Preferably, the acylation reaction is carried out in toluene in the presence of zinc.

Alternatively, compound of the formula (II) are reacted with $R^4CH_2CON(CH_3)_2$ (acid dimethyl amides) (where $R^4$ is as defined earlier) in the presence of $POCl_3$ under Vilsmeier-Haackreaction conditions as described in literature (Jeffrey A. Pfefferkorn et al., Tetrahedron 63 (2007) 8124-8134) to obtain the compound of the formula (III) (where $R^1$, $R^2$, $R^3$ and $R^4$ are same as defined earlier). Preferably, the Vilsmeier-Haackreaction is carried out in dichloroethane in the presence of $POCl_3$.

The compound of the formula (III) (where $R^1$, $R^2$, $R^3$ and $R^4$ are same as defined earlier) are reacted with a halogenating reagent such as, but not limited to, bromine, N-bromosuccinimide, N-chlorosuccinimide, and phosphorous tribromide (Elena Dvornikova et al., Synlett, 2002, No. 7, 1152-1154) to obtain the compounds of formula (IV) (where $R^1$, $R^2$, $R^3$ and $R^4$ are same as defined earlier). Preferably, the halogenation reaction is carried out in THF in the presence of N-bromosuccinimide.

The compound of formula (IV) so obtained in the previous step are subjected to Suzuki coupling with boronic acids or esters represented by formula (V), (where $R^5$, $R^6$, $R^7$ and m are as defined earlier) to obtain compounds of formula (I) (where $R^1$, $R^2$, $R^3$, $R^4$, $R^5$, $R^6$, $R^7$ and m are as defined earlier). Suzuki coupling with boronic acids and esters can be carried out by following procedures well known in the art. Preferably, the Suzuki coupling is carried out in a mixture of ethanol and toluene, in the presence of a base such as potassium phosphate, potassium carbonate or the like, and tetrakis(triphenylphosphine)palladium(0) at a temperature of about 50° C. or higher. Boronic acid used in this reaction can be prepared by methods well known in the art by hydrolyzing the corresponding boronate. Boronates are generally commercially available. Besides, such boronates can also be prepared by reacting an appropriate iodo- or bromo compound with an alkyl lithium such as butyl lithium and then reacting with a borate ester or by other methods well known in the art (Review article by N. Miyaura and A. Suzuki, Chem. Rev., 1995, 95, 2457-2483).

The intermediates and the compounds of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting them to one of the purification methods, such as column chromatography (e.g., flash chromatography) on a suitable support material such as alumina or silica gel using an eluent such as dichloromethane, ethyl acetate, hexane, methanol, acetone and their combinations. Preparative LC-MS method is also used for the purification of the molecules described herein.

Salts of the compound of formula (I) can be obtained by dissolving the compounds in a suitable solvent, for example in a chlorinated hydrocarbon, such as methylene chloride or chloroform or a low molecular weight aliphatic alcohol, for example, ethanol or isopropanol, which is then treated with the desired acid or base as described by Stephen M. Berge, et al. "Pharmaceutical Salts," a review article in Journal of Pharmaceutical sciences, 1977, 66 (1), 1-19 and in the Handbook of Pharmaceutical Salts, Properties, Selection, and Use, by P. Heinrich Stahland Camille G. Wermuth, Wiley-VCH (2002). Lists of suitable salts can also be found in Remington's Pharmaceutical Sciences, 18th ed., Mack Publishing Company, Easton, Pa., 1990, p. 1445, and Stephen M. Berge et al., Journal of Pharmaceutical Science, 1977, 66 (1), 1-19. For example, they can be a salt of an alkali metal (e.g., sodium or potassium), alkaline earth metal (e.g., calcium), or an ammonium salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compound of formula (I) of the present invention may be prepared by stereospecific syntheses or resolution of the achiral compound using an optically active amine, acid or complex forming agent, and separating the diastereomeric salt/complex by fractional crystallization or by columnchromatography.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted- or unsubstituted-, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, optionally substituted, e.g., with methyl, halo, or methoxy substituents aryl and aryl-lower alkyl esters, amides, lower-alkyl amides, di-lower alkyl amides, and hydroxy amides.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In accordance with the invention, modulation of the nicotinic cholinergic receptors, particularly α7, provides for efficacy in a range of cognitive states, right from pre-attention to attention and subsequently working, reference and recognition memory. Accordingly, the present invention finds application in the treatment and prophylaxis of a multitude of diseases or conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Morten S. Thomsen, et al., Current Pharmaceutical Design, 2010, 16, 323-343; Peng Zhi-Zhen et al., Zhonghua Yi Xue Yi Chuan Xue Za Zhi, 2008, 25, 154-158; Jared W. Young, et al., European Neuropsychopharmacology, (2007), 17, 145-155; Laura F. Martin, et al., American Journal of Medical Genetics, Part B (Neuropsychiatric Genetics), 2007, 144B, 611-614; Laura F. Martin, et al., Psychopharmacology, (2004), 174, 54-64; Agnes Feher, et al., Dement. Geriatr. Cogn. Disord., 2009, 28, 56-62; Timothy E. Wilens, et al., Biochem. Pharmacol., 2007, 74 (8), 1212-1223; S. L. Verbois, et al., Neuropharmacology, 44 (2003), 224-233; Paul R. Sanberg, et al., Pharmacol. Ther., 1997, 74 (1), 21-25). The cholinergic system, particularly through α7 nAChR, also has implications in traumatic brain injury-induced psychosis. Accordingly, the present invention also finds application in the treatment of deficits in cholinergic α7 nAChR following traumatic brain injury.

Modulation of nicotinic ACh receptors, particularly the α7 subtype also helpsto supplement the down-regulated cholinergic receptor expression and transmission as in dementia(s), and also in slowing disease progression by reduction of the α7-α$β_{1-42}$ complexation and internalization in AD and Down's syndrome (Agneta Nordberg, et al., Neurotoxicity Research, 2000, 2, 157-165; Simon N. Haydar et al., Bioorganic & Medicinal Chemistry, 17 (2009), 5247-5258; Stephen I. Deutsch et al., Clinical Neuropharmacology, 2003, 26 (5), 277-283).

The compounds of the invention also find application in the treatment and prophylaxis of a multitude of diseases or conditions including, either one or combinations of, dementia(s) due to Alzheimer's disease, dementia with Lewy bodies, or dementia due to Down's syndrome, head trauma, Stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, drugs, alcohol, lead, mercury, aluminium, heavy metals, syphilis, Lyme disease, viral encephalitis, fungal infection and cryptococcosis (Xilong Zhao et al., Annals New York Academy Science, 2001, 939, 179-186; Elaine Perry et al., European Journal of Pharmacology, 393 (2000), 215-222; C. R. Harrington et al., Dementia, 1994, 5, 215-228; Juan Wang et al., Journal of Neuroscience Research, 88, 807-815 (2010); Kamil Duris et al., Stroke, 2011, 42(12), 3530-3536). The compounds of the present invention also find application in the prophylaxis and preventive measures immediately after early-stage identification of neurodegenerative disease like Alzheimer's disease and Parkinson's disease.

Modulation of nicotinic ACh receptors particularly α4β2, α3β4 and α7 also has implications in the development of therapies for nicotine or cannabis addiction and relapse prevention. Accordingly, compounds of the invention find application in the prophylaxis or therapy of nicotine addiction, cannabis addiction, and relapse prevention of nicotine or cannabis addiction. Additionally, this invention further provides an alternative therapy for non-responding addiction patients, patients having intolerable side-effects with de-addiction therapies or those requiring long-term maintenance therapies. (Alexander Kuzmin et al., Psychopharmacology, (2009), 203, 99-108; Robert B. Weiss et al., PLoS Genetics, 2008, 4 (7), e1000125; Marcello Solinas et al., The Journal of Neuroscience, 2007, 27 (21), 5615-5620; Jon 0 Ebbert et al., Patient Preference and Adherence, 2010, 4, 355-362).

The compounds of the invention also find application in the treatment and prophylaxis of a multitude of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Diana L. Donnelly-Roberts et al., Journal of Pharmacologyand Experimental Therapeutics, 1998, 285, 777-786; T. J. Rowley et al., British Journal of Anesthesia, 105 (2), 201-207, (2010); A. Brachfeld et al., Journal of Internal Medicine, 2010, 268, 94-101).

The compounds of the invention also find application in the treatment and prophylaxis of a number of inflammation and pain related states involving TNF-α and providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveititis, contact dermatitis, obesity-related diseases, and endotoxemia (Ida A. J. Giebelen et al., Shock, 2007, 27 (4), 443-447; Pena Geber et al., Eur. J. Immunol., 2010, 40, 2580-2589).

The invention provides a method of preventing or treating a disease or its symptoms or a disorder mediated partially or completely by nicotinic acetylcholine receptors, said method comprising administering to a subject having or susceptible to said disease or its symptoms or disorder with a therapeutically effective amount of a compound of formula (I), its tautomeric forms, its stereoisomers, or its pharmaceutically acceptable salts.

The disorder, condition, and disease as described above are selected from Alzheimer's disease, mild cognitive impairment, senile dementia, vascular dementia, dementia of Parkinson's disease, attention deficit disorder, attention deficit hyperactivity disorder, dementia associated with Lewy bodies, AIDS dementia complex, Picks disease, dementia associated with Down's syndrome, Huntington's disease, cognitive deficits associated with traumatic brain injury, cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The disease, disorder and condition as described above are particularly selected from the group classified or diagnosed as major or minor neurocognitive disorders, or disorders arising due to neurodegeneration.

The invention further provides a method comprising administering a compound of formula (I) in combination with or as adjunct to medications utilized in the treatment of attention deficit hyperactivity disorders, schizophrenia, cognitive disorders such as Alzheimer's disease, Parkinson's dementia, vascular dementia or dementia associated with Lewy bodies, or traumatic brain injury. The medications can be administered simultaneously, sequentially, or cyclically with a compound of formula (I).

The invention further provides a method comprising administering a compound of formula (I) in combination with or as an adjunct to other medications, for example, acetylcholinesterase inhibitors, disease modifying drugs or biologics for neurodegenerative disorders, dopaminergic drugs, antidepressants, or a typical or atypical antipsychotic. The other medications can be administered simultaneously, sequentially, or cyclically with a compound of formula (I).

The invention also provides for the use of a compound of formula (I), its tautomeric forms, its stereoisomers, and its pharmaceutically acceptable salts in the preparation of a medicament for preventing or treating a disease or its symptoms or a disorder mediated partially or completely by nicotinic acetylcholine receptors.

In the use described above, the disease or disorder or condition is selected from the group classified or diagnosed as major or minor neurocognitive disorders, or disorders arising due to neurodegeneration.

The use described above is in combination with or as adjunct to medications utilized in the treatment of attention deficit hyperactivity disorders, schizophrenia, cognitive disorders, Alzheimer's disease, Parkinson's dementia, vascular dementia or dementia associated with Lewy bodies, and traumatic brain injury.

The use described above is in combination with or as an adjunct to acetylcholinesterase inhibitors, disease modifying drugs or biologics for neurodegenerative disorders, dopaminergic drugs, antidepressants, or a typical or atypical antipsychotic.

The terms "treat" or "prevent," as well as words stemming therefrom, as used herein, do not necessarily imply 100% or complete treatment or prevention. Rather, there are varying degrees of treatment and prevention of which one of ordinary skill in the art recognizes as having a potential benefit or therapeutic effect. In this respect, the inventive methods can provide any amount of any level of treatment or prevention of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment or prevention provided by the inventive method can include treatment or prevention of one or more conditions or symptoms of the disorder. Also, for purposes herein, "treatment" or "prevention," can encompass delaying the onset of the disorder, or a symptom or condition thereof.

Following are the abbreviations used and meaning thereof in the specification:

AIDS: Acquired Immunodeficiency Syndrome.

HBSS: Hanks Balanced Salt Solution.

HEPES: 4-(2-hydroxyethyl)piperazine-1-ethanesulfonic acid.

THF: Tetrahydrofuran.

TLC: Thin Layer Chromatography.

NMR: Nuclear Magnetic Resonance.

α7 nAChR: nicotinic acetylcholine receptor α7 subunit.

Following examples are provided to further illustrate the present invention and therefore should not be construed in any way to limit the scope of the present invention.

All $^1$HNMR spectra were determined in the solvents indicated and chemical shifts are reported in δ units downfield from the internal standard tetramethylsilane (TMS) and interproton coupling constants are reported in Hertz (Hz).

EXAMPLE 1

Preparation of 4-(1-(4-chlorophenyl)-4-(2-cyclopropylacetyl)-2,5-dimethyl-1H-pyrrol-3-yl)benzenesulfonamide (Compound 1)

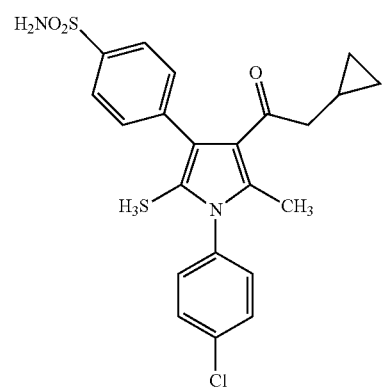 [SMILES: Cc1c(C(=O)CC2CC2)c(-c2ccc(S(N)(=O)=O)cc2)c(S)n1-c1ccc(Cl)cc1]

Step 1: 1-(1-(4-chlorophenyl)-2,5-dimethyl-1H-pyrrol-3-yl)-2-cyclopropylethanone (Compound 1a)

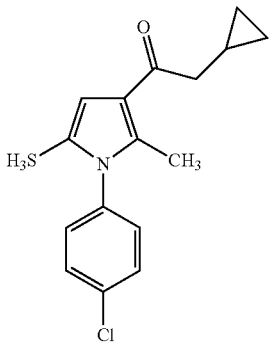

Cyclopropylacetyl chloride (1.17 g, 9.92 mmol) was added to a stirred solution of 1-(4-chlorophenyl)-2,5-dimethyl-1H-pyrrole (prepared according to the procedure given in Synthetic Communications, 2009, 39, 23, 4180-4198) (1.70 g, 8.27 mmol) and Zinc (1.08 g, 16.53 mmol) in toluene (15 ml) at 25° C. The reaction mixture was stirred at 25° C. for 2.5 h. The progress of the reaction was monitored by TLC. The mixture was diluted with saturated solution of sodium bicarbonate (30 ml), and the resulting aqueous and organic phases were separated. The aqueous layer was extracted with ethyl acetate (3×50 ml). The combined organic layer was washed with water (1×30 ml) and dried over anhydrous $Na_2SO_4$. The solvent was evaporated under reduced pressure to obtain a crude product. This crude product was purified by column chromatography using 10% ethyl acetate in hexanes as an eluent to obtain compound 1a (0.85 g, 35.7%). MS: m/z 288 (M+1).

$^1$HNMR (CDCl$_3$, 400 MHz): δ 7.49 (d, J=8.4 Hz, 2H), 7.14 (d, J=8.4 Hz, 2H), 6.30 (s, 1H), 2.67 (d, J=6.8 Hz, 2H), 2.34 (s, 3H), 1.97 (s, 3H), 1.16-1.20 (m, 1H), 0.56-0.61 (m, 2H), 0.18-0.22 (m, 2H).

Step 2: 1-(4-bromo-1-(4-chlorophenyl)-2,5-dimethyl-1H-pyrrol-3-yl)-2-cyclopropylethanone (Compound 1b)

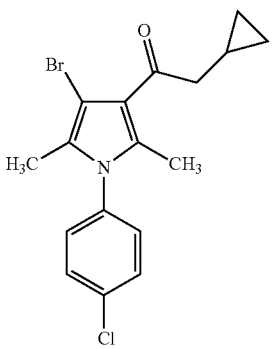 [SMILES: Cc1c(Br)c(C(=O)CC2CC2)c(C)n1-c1ccc(Cl)cc1]

To a stirred solution of 1-(1-(4-chlorophenyl)-2,5-dimethyl-1H-pyrrol-3-yl)-2-cyclopropylethanone (Compound 1a, 0.85 g, 2.95 mmol) in THF (15 ml) at −78° C. was added a solution of N-bromosuccinimide (0.58 g, 3.25 mmol) in THF (10.0 ml) in a drop wise manner. The resulting mixture was stirred at −78° C. for 10 min. The progress of the reaction was monitored by TLC. The reaction mixture was quenched by the addition of saturated sodium bicarbonate solution (10 ml). The solvent was evaporated under reduced pressure and the residue was dissolved in ethyl acetate (50 ml). The organic layer was washed with saturated sodium bicarbonate solution (1×10 ml) followed by water (1×10 ml). The combined organic layer was dried over anhydrous $Na_2SO_4$. The solvent was evaporated under reduced pressure to obtain a crude product, which was purified by flash column chromatography using 15% ethyl acetate in hexanes to obtain the title compound 1b (0.60 g, 55.4%). MS: m/z 368 (M+1).

$^1$HNMR (CDCl$_3$, 400 MHz): δ 7.52 (d, J=8.4 Hz, 2H), 7.13 (d, J=8.4 Hz, 2H), 2.95 (d, J=6.8 Hz, 2H), 2.27 (s, 3H), 2.00 (s, 3H), 1.16-1.22 (m, 1H), 0.57-0.60 (m, 2H), 0.19-0.22 (m, 2H).

Step 3: 4-(1-(4-chlorophenyl)-4-(2-cyclopropylacetyl)-2,5-dimethyl-1H-pyrrol-3-yl)benzenesulfonamide (Compound 1)

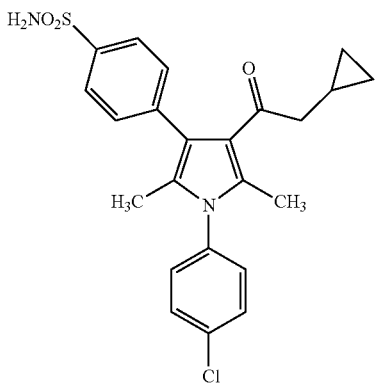 [SMILES: Cc1c(C(=O)CC2CC2)c(-c2ccc(S(N)(=O)=O)cc2)c(C)n1-c1ccc(Cl)cc1]

4-aminosulfonylbenzene boronic acid (0.18 g, 0.88 mmol) and potassium carbonate (0.20 g, 1.47 mmol) were added to a solution of 1-(4-bromo-1-(4-chlorophenyl)-2,5-dimethyl-1H-pyrrol-3-yl)-2-cyclopropylethanone (Compound 1b, 0.27 g, 0.74 mmol) in a mixture of toluene:ethanol (3:9 ml) in a tube at 25° C. Nitrogen gas was bubbled through the resulting mixture for 15 minutes. Tetrakis(triphenylphosphine)palladium(0) (0.043 g, 0.037 mmol) was added to the reaction mixture under nitrogen atmosphere and the tube was sealed. The reaction mixture was heated at 90-95° C. for 5 hr under stirring. The progress of the reaction was monitored by TLC. The reaction mixture was cooled to 25° C. and filtered through celite. The residue was washed with mixture of 10% methanol in dichloromethane. The filtrate was concentrated under reduced pressure to obtain a crude product, which was purified by flash column chromatography using 40% ethyl acetate in hexanes as an eluent to obtain the title compound 1 (0.12 g, 36.8%). MS: m/z 443 (M+1).

$^1$HNMR (DMSO-d$_6$, 400 MHz): δ 7.85 (d, J=8.4 Hz, 2H), 7.65 (d, J=8.4 Hz, 2H), 7.47 (d, J=8.4 Hz, 2H), 7.39-7.43 (m, 4H), 2.17-2.19 (m, 5H), 1.83 (s, 3H), 0.82-0.89 (m, 1H), 0.32-0.37 (m, 2H), 0.11-0.13 (m, 2H).

The following compounds were prepared according to the procedure described above for compound 1, with appropriate changes to the reactants.

4-(1-(4-chlorophenyl)-2,5-dimethyl-4-(2-(2-oxopyrrolidin-1-yl)acetyl)-1H-pyrrol-3-yl)benzenesulfonamide (Compound 2). MS: m/z 486 (M+1).

¹HNMR (DMSO-d₆, 400 MHz): δ 7.86 (d, J=8.4 Hz, 2H), 7.67 (d, J=8.4 Hz, 2H), 7.38-7.40 (m, 6H), 3.87-3.89 (m, 2H), 3.16-3.18 (m, 2H), 2.20-2.24 (m, 5H), 1.81-1.89 (m, 5H).

4-(1-(4-chlorophenyl)-2,5-dimethyl-4-(2-(pyrrolidin-1-yl)acetyl)-1H-pyrrol-3-yl)benzenesulfonamide (Compound 3). MS: m/z 472 (M+1).

¹HNMR (CDCl₃, 400 MHz): δ 8.01 (d, J=8.4 Hz, 2H), 7.65 (d, J=8.4 Hz, 2H), 7.53 (d, J=8.4 Hz, 2H), 7.36 (d, J=8.0 Hz, 2H), 4.89 (bs-exchanges with D₂O, 2H), 3.91-3.93 (m, 2H), 3.14-3.16 (m, 4H), 2.36 (s, 3H), 1.83-1.85 (m, 4H), 1.85 (s, 3H).

4-(1-(4-chlorophenyl)-4-(2-cyclobutylacetyl)-2,5-dimethyl-1H-pyrrol-3-yl)-2-fluorobenzenesulfonamide (Compound 6). MS: m/z 475 (M+1).

¹HNMR (DMSO-d₆, 400 MHz): δ 7.79 (t, J=8.0 Hz, 1H), 7.69 (bs-exchanges with D₂O, 2H), 7.64 (d, J=8.8 Hz, 2H), 7.45 (d, J=8.8 Hz, 2H), 7.26 (dd, J=8.4, 1.6 Hz, 1H), 7.18 (dd, J=8.4, 1.6 Hz, 1H), 2.46-2.51 (m, 2H), 2.15 (s, 3H), 1.89-1.91 (m, 3H), 1.85 (s, 3H), 1.73-1.75 (m, 2H), 1.45-1.47 (m, 2H).

4-(1-(4-chloro-3-methylphenyl)-4-(2-cyclopropylacetyl)-2,5-dimethyl-1H-pyrrol-3-yl)benzenesulfonamide (Compound 7). MS: m/z 458 (M+1).

¹HNMR (DMSO-d₆, 400 MHz): δ 7.83 (d, J=8.4 Hz, 2H), 7.62 (d, J=8.4 Hz, 1H), 7.28-7.39 (m, 5H), 7.36 (d, J=8.4 Hz, 1H), 2.40 (s, 3H), 2.16-2.18 (m, 5H), 1.83 (s, 3H), 0.85-0.87 (m, 1H), 0.32-0.35 (m, 2H), −0.14 to −0.11 (m, 2H).

4-(1-(4-chlorophenyl)-4-(2-cyclopropylacetyl)-2,5-dimethyl-1H-pyrrol-3-yl)-2-fluorobenzenesulfonamide (Compound 8). MS: m/z 461 (M+1).

¹HNMR (DMSO-d₆, 400 MHz): δ 7.79 (t, J=8.0 Hz, 1H), 7.68 (bs-exchanges with D₂O, 2H), 7.66 (d, J=8.4 Hz, 2H), 7.46 (d, J=8.4 Hz, 2H), 7.25 (t, J=8.0 Hz, 1H), 7.19 (t, J=8.0 Hz, 1H), 2.26 (d, J=6.8 Hz, 2H), 2.18 (s, 3H), 1.85 (s, 3H), 0.87-0.89 (m, 1H), 0.35-0.38 (m, 2H), −0.09 to −0.07 (m, 2H).

4-(1-(4-chlorophenyl)-4-(2-cyclobutylacetyl)-2,5-dimethyl-1H-pyrrol-3-yl)benzenesulfonamide (Compound 9). MS: m/z 457 (M+1).

¹HNMR (DMSO-d₆, 400 MHz): δ 7.84 (d, J=8.4 Hz, 2H), 7.65 (d, J=8.4 Hz, 2H), 7.40-7.46 (m, 6H), 2.37 (d, J=6.8 Hz, 2H), 2.15 (s, 3H), 1.84-1.86 (m, 2H), 1.83 (s, 3H), 1.66-1.71 (m, 3H), 1.40-1.43 (m, 2H).

4-(1-(4-chlorophenyl)-2-cyclopropyl-4-(2-cyclopropylacetyl)-5-methyl-1H-pyrrol-3-yl)benzenesulfonamide (Compound 10). MS: m/z 470 (M+1).

¹HNMR (CDCl₃, 400 MHz): δ 7.98 (d, J=8.4 Hz, 2H), 7.39-7.48 (m, 4H), 7.21 (d, J=8.4 Hz, 2H), 4.89 (bs-exchanges with D₂O, 2H), 2.40 (d, J=6.8 Hz, 2H), 2.27 (s, 3H), 1.56-1.57 (m, 1H), 1.27-1.29 (m, 1H), 0.44-0.46 (m, 4H), −0.02 to −0.04 (m, 2H), −0.06 to −0.05 (m, 2H).

4-(1-(4-chloro-3-methylphenyl)-4-(2-cyclopropylacetyl)-2,5-dimethyl-1H-pyrrol-3-yl)-2-fluorobenzenesulfonamide (Compound 11). MS: m/z 476 (M+1).

¹HNMR (DMSO-d₆, 400 MHz): δ 7.78 (t, J=8.0 Hz, 1H), 7.69 (bs-exchanges with D₂O, 2H), 7.62 (d, J=8.4 Hz, 1H), 7.45 (d, J=2.0 Hz, 1H), 7.17-7.28 (m, 3H), 2.40 (s, 3H), 2.24 (d, J=6.8 Hz, 2H), 2.18 (s, 3H), 1.85 (s, 3H), 0.89-0.91 (m, 1H), 0.35-0.38 (m, 2H), −0.09 to −0.08 (m, 2H).

4-(1-(4-chlorophenyl)-4-(2-cyclopropylacetyl)-5-methyl-2-(trifluoromethyl)-1H-pyrrol-3-yl)benzenesulfonamide (Compound 15). MS: m/z 497 (M+1).

¹HNMR (CDCl₃, 400 MHz): δ 7.79 (d, J=8.4 Hz, 2H), 7.28-7.36 (m, 4H), 6.99 (d, J=8.4 Hz, 2H), 4.89 (bs-exchanges with D₂O, 2H), 2.79 (d, J=6.8 Hz, 2H), 2.19 (s, 3H), 1.17-1.19 (m, 1H), 0.59-0.63 (m, 2H), 0.20-0.22 (m, 2H).

EXAMPLE 2

Preparation of 4-(1-(4-chlorophenyl)-4-(2-cyclopentylacetyl)-2,5-dimethyl-1H-pyrrol-3-yl)benzenesulfonamide (Compound 12)

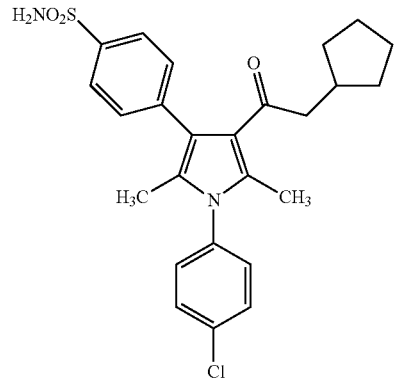

Step 1: 1-(1-(4-chlorophenyl)-2,5-dimethyl-1H-pyrrol-3-yl)-2-cyclopentylethanone (Compound 12a)

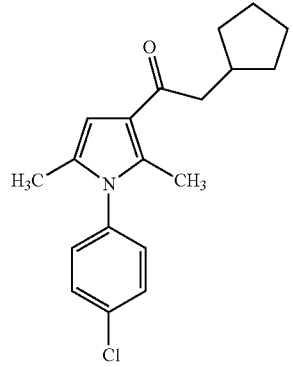 [SMILES: Cc1cc(C(=O)CC2CCCC2)c(C)n1-c1ccc(Cl)cc1]

POCl₃ (0.82 g, 0.59 ml, 5.35 mmol) was added to 2-cyclopentyl-N,N-dimethylacetamide (0.83 g, 5.35 mmol) at 0° C. and under stirring. Stirring was continued at 0° C. for 15 min. The reaction mixture was allowed to come at room temperature, stirred for 20 min, and diluted with 1,2-dichloroethane (20 ml). 2-(4-chlorophenyl)-1,3-dimethyl-1H-pyrrole (prepared according to the procedure described in Tetrahedron Letters 46 (2005) 4539-4542; 1.00 g, 4.86 mmol) was dissolved in 1,2-dichloroethane (20 ml) and was added to the reaction mixture at 0° C. The reaction mixture was heated to reflux temperature (95° C.) for 30 min. The progress of the reaction was monitored by TLC. The reaction mixture was cooled to room temperature. Sodium acetate (3.64 g, 26.7 mmol) was dissolved in water (50 ml) and added to the reaction mixture. The reaction mixture was stirred at 80° C. for 30 min. Progress of the reaction was monitored by TLC. The reaction mixture was cooled to room temperature, diluted with DCM (50 ml), and water (20 ml) was added to it. The organic layer was separated, dried over anhydrous sodium sulfate, filtered, and concentrated to obtain a crude product. This crude product was purified by column chromatography using 5-10% ethyl acetate in hexanes as an eluent to obtain the title compound 12a (0.95 g, 61.9%). MS: m/z 316 (M+1).

$^1$HNMR (CDCl$_3$, 400 MHz): δ 7.50 (d, J=8.8 Hz, 2H), 7.15 (d, J=8.8 Hz, 2H), 6.34 (s, 1H), 2.77 (d, J=6.8 Hz, 2H), 2.34-2.36 (m, 1H), 2.32 (s, 3H), 2.00 (s, 3H), 1.86-1.88 (m, 2H), 1.55-1.65 (m, 4H), 1.18-1.22 (m, 2H).

Step 2: 1-(4-bromo-1-(4-chlorophenyl)-2,5-dimethyl-1H-pyrrol-3-yl)-2-cyclopentylethanone (Compound 12b)

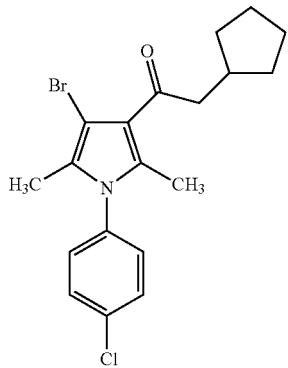 [SMILES: Cc1c(Br)c(C(=O)CC2CCCC2)c(C)n1-c1ccc(Cl)cc1]

To a stirred solution of 1-(1-(4-chlorophenyl)-2,5-dimethyl-1H-pyrrol-3-yl)-2-cyclopentylethanone (Compound 12a, 0.95 g, 3.01 mmol) in THF (15 ml) at −78° C. was added a solution of N-bromosuccinimide (0.64 g, 3.61 mmol) in THF (15.0 ml) in a drop wise manner. The resulting mixture was stirred at −78° C. for 10 min. The progress of reaction was monitored by TLC. The reaction mixture was quenched by addition of water (10 ml) and extracted with ethyl acetate (2×25 ml). The organic layer was washed with water (1×10 ml) and dried over anhydrous Na$_2$SO$_4$. The solvent was evaporated under reduced pressure to obtain a crude product, which was purified by flash column chromatography using 2-5% ethyl acetate in hexanes to obtain the title compound 12b (0.80 g, 67.4%). MS: m/z 396 (M+1).

$^1$HNMR (CDCl$_3$, 400 MHz): δ 7.51 (d, J=8.8 Hz, 2H), 7.11 (d, J=8.8 Hz, 2H), 3.03 (d, J=6.8 Hz, 2H), 2.36-2.39 (m, 1H), 2.23 (s, 3H), 2.06 (s, 3H), 1.84-1.86 (m, 2H), 1.54-1.65 (m, 4H), 1.19-1.22 (m, 2H).

Step 3: 4-(1-(4-chlorophenyl)-4-(2-cyclopentylacetyl)-2,5-dimethyl-1H-pyrrol-3-yl)benzenesulfonamide (Compound 12)

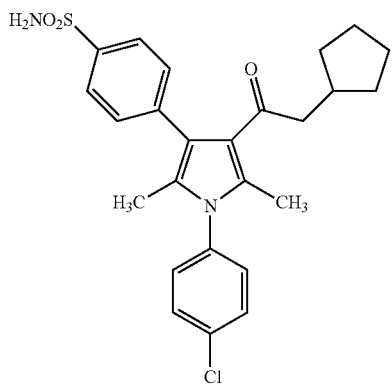 [SMILES: Cc1c(C(=O)CC2CCCC2)c(-c2ccc(S(N)(=O)=O)cc2)c(C)n1-c1ccc(Cl)cc1]

4-aminosulfonylbenzene boronic acid (0.49 g, 2.43 mmol) and potassium carbonate (0.42 g, 3.04 mmol) were added to a solution of 1-(4-bromo-1-(4-chlorophenyl)-2,5-dimethyl-1H-pyrrol-3-yl)-2-cyclopentylethanone (Compound 12b, 0.80 g, 2.02 mmol) in a mixture of toluene:ethanol (2:8 ml) in a tube at 25° C. Nitrogen gas was bubbled through the resulting mixture for 15 minutes. Tetrakis(triphenylphosphine)palladium(0) (0.12 g, 0.10 mmol) was added to the reaction mixture under nitrogen atmosphere and the tube was sealed. The reaction mixture was heated at 100° C. for 4 hr under stirring. The progress of the reaction was monitored by TLC. The reaction mixture was cooled to 25° C. and filtered through celite. The filtrate was concentrated under reduced pressure to obtain a crude product, which was purified by flash column chromatography using 40% ethyl acetate in hexanes as an eluent to obtain the title compound 12 (0.36 g, 37.7%). MS: m/z 471 (M+1).

$^1$HNMR (CDCl$_3$, 400 MHz): δ 7.94 (d, J=8.4 Hz, 2H), 7.53 (d, J=8.8 Hz, 2H), 7.41 (d, J=8.4 Hz, 2H), 7.21 (d, J=8.8 Hz, 2H), 4.94 (bs-exchanges with D$_2$O, 2H), 2.27 (d, J=6.8 Hz, 2H), 2.24 (s, 3H), 2.16-2.18 (m, 1H), 1.88 (s, 3H), 1.65-1.67 (m, 2H), 1.44-1.47 (m, 4H), 0.86-0.89 (m, 2H).

The following compounds were prepared according to the procedure described above for compound 12, with appropriate changes to the reactants.

4-(4-(2-cyclopropylacetyl)-1-(4-(dimethylamino)phenyl)-2,5-dimethyl-1H-pyrrol-3-yl)benzenesulfonamide (Compound 4). MS: m/z 452 (M+1).

$^1$HNMR (DMSO-d$_6$, 400 MHz): δ 7.81 (d, J=8.4 Hz, 2H), 7.38-7.42 (m, 4H), 7.15 (d, J=8.4 Hz, 2H), 6.82 (d, J=8.4 Hz, 2H), 2.97 (s, 6H), 2.14-2.17 (m, 5H), 1.81 (s, 3H), 0.84-0.87 (m, 1H), 0.31-0.35 (m, 2H), −0.13 to −0.11 (m, 2H).

4-(4-(2-cyclopropylacetyl)-1-(4-fluorophenyl)-2,5-dimethyl-1H-pyrrol-3-yl)benzenesulfonamide (Compound 5). MS: m/z 427 (M+1).

$^1$HNMR (DMSO-d$_6$, 400 MHz): δ 7.84 (d, J=8.4 Hz, 2H), 7.41-7.47 (m, 8H), 2.16-2.99 (m, 5H), 1.83 (s, 3H), 0.84-0.87 (m, 1H), 0.33-0.36 (m, 2H), −0.13 to −0.11 (m, 2H).

4-(1-(4-chlorophenyl)-4-(2-cyclopentylacetyl)-2,5-dimethyl-1H-pyrrol-3-yl)-2-fluorobenzenesulfonamide (Compound 13). MS: m/z 488 (M+1).

$^1$HNMR (CDCl$_3$, 400 MHz): δ 7.92 (t, J=8.0 Hz, 1H), 7.53 (d, J=8.4 Hz, 2H), 7.13-7.21 (m, 4H), 5.12 (bs-exchanges with D$_2$O, 2H), 2.36 (d, J=6.8 Hz, 2H), 2.23 (s, 3H), 2.19-2.21 (m, 1H), 1.89 (s, 3H), 1.66-1.68 (m, 2H), 1.46-1.52 (m, 4H), 0.87-0.89 (m, 2H).

4-(1-(4-chlorophenyl)-4-(2-cyclopropylacetyl)-5-ethyl-2-methyl-1H-pyrrol-3-yl)benzenesulfonamide (Compound 14). MS: m/z 457 (M+1).

$^1$HNMR (DMSO-d$_6$, 400 MHz): δ 7.91 (d, J=8.4 Hz, 2H), 7.58 (d, J=8.4 Hz, 2H), 7.49 (d, J=8.4 Hz, 2H), 7.34-7.41 (m, 4H), 2.64 (q, J=6.8 Hz, 2H), 2.24 (d, J=7.2 Hz, 2H), 1.89 (s, 3H), 1.03 (t, J=6.8 Hz, 3H), 0.86-0.88 (m, 1H), 0.36-0.39 (m, 2H), −0.08 to −0.06 (m, 2H).

4-(1-cyclohexyl-4-(2-cyclopropylacetyl)-2,5-dimethyl-1H-pyrrol-3-yl)benzenesulfonamide (Compound 16). MS: m/z 415 (M+1).

$^1$HNMR (DMSO-d$_6$, 400 MHz): δ 7.80 (d, J=8.4 Hz, 2H), 7.38 (bs-exchanges with D$_2$O, 2H), 7.31 (d, J=8.4 Hz, 2H), 4.09-4.12 (m, 1H), 2.47 (s, 3H), 2.12 (s, 3H), 1.97-1.99 (m, 4H), 1.83 (m, 4H), 1.66-1.68 (m, 1H), 1.41-1.43 (m, 2H), 1.21-1.23 (m, 1H), 0.76-0.78 (m, 1H), 0.26-0.29 (m, 2H), −0.23 to −0.19 (m, 2H).

4-(4-(2-cyclopropylacetyl)-2,5-dimethyl-1-(pyridin-3-yl)-1H-pyrrol-3-yl)benzenesulfonamide (Compound 17). MS: m/z 410 (M+1).

$^1$H NMR (DMSO-d$_6$, 400 MHz): δ 8.75 (d, J=8.0 Hz, 1H), 8.67 (d, J=3.0 Hz, 1H), 7.96-7.98 (m, 1H), 7.95 (d, J=8.4 Hz, 2H), 7.66-7.68 (m, 1H), 7.46 (bs-exchanges with D$_2$O, 2H), 7.42 (d, J=8.4 Hz, 2H), 2.17-2.19 (m, 5H), 1.85 (s, 3H), 0.86-0.88 (m, 1H), 0.34-0.37 (m, 2H), −0.15 to −0.11 (m, 2H).

4-(4-(2-cyclopropylacetyl)-2,5-dimethyl-1-(1-methylpiperidin-4-yl)-1H-pyrrol-3-yl)benzenesulfonamide (Compound 18). MS: m/z 430 (M+1).

$^1$H NMR (DMSO-d$_6$, 400 MHz): δ 7.81 (d, J=8.4 Hz, 2H), 7.31-7.39 (m, 4H), 4.06-4.11 (m, 1H), 2.88-2.90 (m, 2H), 2.47 (s, 3H), 1.98-2.21 (m, 12H), 1.77-1.79 (m, 2H), 0.76-0.78 (m, 1H), 0.26-0.29 (m, 2H), −0.23 to −0.19 (m, 2H).

EXAMPLE 3

Pharmacological Screening

The compounds were tested in a cell-based real-time kinetic assay in human IMR-32 cells with native expression of α7 nAChR. The increase in intracellular Ca$^{2+}$ levels was measured in a Fluorometric Imaging Plate Reader (FLIPR). Test compound solutions and agonist solutions were made in assay buffer (HBSS, pH 7.4, 20 mM HEPES, and 10 mM CaCl$_2$). Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For the evaluation of compound mediated potentiation of agonist response, growth media was removed from the wells and 200 µl of FLIPR calcium 4 dye (Molecular Devices), reconstituted in assay buffer, and added to the wells. After dye loading, the microplates were incubated for 30 min at 37° C. and 30 min at room temperature and then directly transferred to the FLIPR. Baseline fluorescence was monitored for the first 10 to 30 s followed by the addition of 25 µl of the test compound solution and subsequent monitoring of fluorescence changes for up to 10 min. This was followed by addition of 25 µl of agonist solution (PNU-282987, 10 µM) and measurement of fluorescence for 4 min. (Ramin Faghih et al. Journal of Medicinal Chemistry, 2009, 52, 3377-3384).

The compound-induced fold increase in agonist response (fold PAM activity) was computed by dividing the maximum effect (Max-Min fluorescence) obtained with the test compound in presence of agonist with the agonist-alone effect. EC$_{50}$ of the compound was calculated using GraphPad Prism software version 5.0, by plotting compound concentrations against fold PAM activity.

Fold activity at 1 µM concentration: the compounds with activity between 1 to 5 folds are grouped as A, the compounds with activity between 5.1 folds and 15 folds are grouped as B and the compounds with activity above 15 folds are grouped as C.

Table 1 provides the fold activity of the compounds of the present invention.

TABLE 1

| Sr. No. | Fold activation at 1 µM conc. (Group) | Compound No. |
|---|---|---|
| 1 | A | 2, 3, 5, 7, 10, 11, 14, 15, 16, 17, 18 |
| 2 | B | 4, 6, 12, 13 |
| 3 | C | 1, 8, 9 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I), a tautomer thereof, a stereoisomer thereof, or a pharmaceutically acceptable salt thereof,

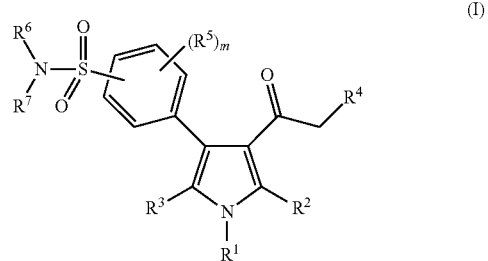

wherein,
R$^1$ is selected from substituted- or unsubstituted-cycloalkyl, and substituted- or unsubstituted-aryl, substituted- or unsubstituted-heteroaryl and substituted- or unsubstituted-heterocyclyl;

R² is selected from substituted- or unsubstituted-alkyl, perhaloalkyl, substituted- or unsubstituted-cycloalkyl, and substituted- or unsubstituted-heterocyclyl;

R³ is selected from substituted- or unsubstituted-alkyl, perhaloalkyl, substituted- or unsubstituted-cycloalkyl, and substituted- or unsubstituted-heterocyclyl;

R⁴ is selected from substituted- or unsubstituted-cycloalkyl, and substituted- or unsubstituted-heterocyclyl;

R⁵ is independently selected at each occurrence from halogen, substituted- or unsubstituted-alkyl, perhaloalkyl, substituted- or unsubstituted-cycloalkyl, —OR$^{7b}$, —NR⁶R⁷, and —C(=O)R$^{7a}$; or two R⁵ groups and the carbon atoms to which they are attached together from 5 to 6 membered carbocycle or 5 to 6 membered heterocycle, the carbocycle or heterocycle is optionally substituted with 1 to 3 substituent (s) independently selected from oxo, halogen, cyano, and alkyl;

R⁶ and R⁷ are independently selected from hydrogen, substituted- or unsubstituted-alkyl, substituted- or unsubstituted-cycloalkyl, and —C(=O)R⁷;

R$^{7a}$ is selected from substituted- or unsubstituted-alkyl, perhaloalkyl, and substituted- or unsubstituted-cycloalkyl;

R$^{7b}$ is selected from hydrogen, substituted- or unsubstituted-alkyl, perhaloalkyl, and substituted- or unsubstituted-cycloalkyl;

m is an integer selected from 0, 1 and 2;

wherein, when the alkyl group is substituted, it is substituted with 1 to 3 substituents independently selected from halogen, perhaloalkyl, cycloalkyl, —OR$^{8b}$, —N(H)R⁸, and —N(alkyl)R⁸;

when the cycloalkyl and the carbocycle groups are substituted, each of them is substituted with 1 to 3 substituents independently selected from halogen, alkyl, perhaloalkyl, —OR$^{8b}$, —N(H)R⁸, and —N(alkyl)R⁸;

when the aryl group is substituted, it is substituted with 1 to 3 substituents independently selected from halogen, nitro, cyano, hydroxy, alkyl, perhaloalkyl, cycloalkyl, heterocyclyl, —O-alkyl, —O-perhaloalkyl, —N(alkyl) alkyl, —N(H)alkyl, —NH₂, —SO₂-alkyl, —SO₂-perhaloalkyl, —N(alkyl)C(=O)alkyl, —N(H)C(=O) alkyl, —C(=O)N(alkyl)alkyl, —C(=O)N(H)alkyl, —C(=O)NH₂, —SO₂N(alkyl)alkyl, —SO₂N(H)alkyl, and —SO₂NH₂;

when the heteroaryl group is substituted, it is substituted with 1 to 3 substituents independently selected from halogen, nitro, cyano, hydroxy, alkyl, perhaloalkyl, —O-alkyl, —O-perhaloalkyl, —N(alkyl)alkyl, —N(H) alkyl, and —NH₂;

when the heterocyclyl group is substituted, it can be substituted either on a ring carbon atom(s) or on a ring hetero atom; when it is substituted on a ring carbon atom(s), it is substituted with 1 to 3 substituents independently selected from halogen, nitro, cyano, oxo, alkyl, perhaloalkyl, OR$^{8b}$; and when the 'heterocyclyl' group is substituted on a ring nitrogen, it is substituted with a substituent selected from alkyl, cycloalkyl, —SO₂alkyl, and —C(=O)R$^{8a}$;

R⁸ is selected from hydrogen, alkyl, and cycloalkyl;

R$^{8a}$ is selected from alkyl, perhaloalkyl, and cycloalkyl; and

R$^{8b}$ is selected from hydrogen, alkyl, perhaloalkyl, and cycloalkyl.

2. The compound of formula (I), a tautomer thereof, a stereoisomer thereof, or a pharmaceutically acceptable salt thereof, as claimed in claim 1, wherein R¹ is selected from substituted- or unsubstituted-cycloalkyl, substituted- or unsubstituted-phenyl, substituted- or unsubstituted-pyridyl, and substituted- or unsubstituted-piperidinyl.

3. The compound of formula (I), a tautomer thereof, a stereoisomer thereof, or a pharmaceutically acceptable salt thereof, as claimed in claim 1, wherein R¹ is selected from 4-fluorphenyl, 4-chlorophenyl, 4-(dimethylamino) phenyl, 4-chloro-3-methylphenyl, cyclohexyl, 3-pyridyl, and N-methylpiperidinyl.

4. The compound of formula (I), a tautomer thereof, a stereoisomer thereof, or a pharmaceutically acceptable salt thereof, as claimed in claim 1, wherein R² is a substituted- or unsubstituted-alkyl.

5. The compound of formula (I), a tautomer thereof, a stereoisomer thereof, or a pharmaceutically acceptable salt thereof, as claimed in claim 1, wherein R² is selected from methyl and ethyl.

6. The compound of formula (I), a tautomer thereof, a stereoisomer thereof, or a pharmaceutically acceptable salt thereof, as claimed in claim 1, wherein R³ is selected from substituted- or unsubstituted-alkyl, perhaloalkyl, and substituted- or unsubstituted-cycloalkyl.

7. The compound of formula (I), a tautomer thereof, a stereoisomer thereof, or a pharmaceutically acceptable salt thereof, as claimed in claim 1, wherein R³ is selected from methyl, trifluoromethyl and cyclopropyl.

8. The compound of formula (I), a tautomer thereof, a stereoisomer thereof, or a pharmaceutically acceptable salt thereof, as claimed in claim 1, wherein R⁴ is selected from substituted- or unsubstituted-cycloalkyl, and substituted- or unsubstituted-pyrrolidinyl.

9. The compound of formula (I), a tautomer thereof, a stereoisomer thereof, or a pharmaceutically acceptable salt thereof, as claimed in claim 1, wherein R⁴ is selected from cyclopropyl, cyclobutyl, cyclopentyl, pyrrolidinyl, and 2-oxopyrrolidinyl.

10. The compound of formula (I), a tautomer thereof, a stereoisomer thereof, or a pharmaceutically acceptable salt thereof, as claimed in claim 1, wherein R⁵ is halogen.

11. The compound of formula (I), a tautomer thereof, a stereoisomer thereof, or a pharmaceutically acceptable salt thereof, as claimed in claim 1, wherein R⁶ and R⁷ are hydrogen.

12. The compound of formula (I), a tautomer thereof, a stereoisomer thereof, or a pharmaceutically acceptable salt thereof, as claimed in claim 1, wherein m is selected from 0 and 1.

13. The compound of formula (I), a tautomer thereof, a stereoisomer thereof, or a pharmaceutically acceptable salt thereof, as claimed in claim 1, wherein the compound is selected from:

4-(1-(4-chlorophenyl)-4-(2-cyclopropylacetyl)-2,5-dimethyl-1H-pyrrol-3-yl)benzenesulfonamide;

4-(1-(4-chlorophenyl)-2,5-dimethyl-4-(2-(2-oxopyrrolidin-1-yl)acetyl)-1H-pyrrol-3-yl)benzenesulfonamide;

4-(1-(4-chlorophenyl)-2,5-dimethyl-4-(2-(pyrrolidin-1-yl)acetyl)-1H-pyrrol-3-yl)benzenesulfonamide;

4-(4-(2-cyclopropylacetyl)-1-(4-(dimethylamino)phenyl)-2,5-dimethyl-1H-pyrrol-3-yl)benzenesulfonamide;

4-(4-(2-cyclopropylacetyl)-1-(4-fluorophenyl)-2,5-dimethyl-1H-pyrrol-3-yl)benzenesulfonamide;

4-(1-(4-chlorophenyl)-4-(2-cyclobutylacetyl)-2,5-dimethyl-1H-pyrrol-3-yl)-2-fluorobenzenesulfonamide;

4-(1-(4-chloro-3-methylphenyl)-4-(2-cyclopropylacetyl)-2,5-dimethyl-1H-pyrrol-3-yl)benzenesulfonamide;

4-(1-(4-chlorophenyl)-4-(2-cyclopropylacetyl)-2,5-dimethyl-1H-pyrrol-3-yl)-2-fluorobenzenesulfonamide;

4-(1-(4-chlorophenyl)-4-(2-cyclobutylacetyl)-2,5-dimethyl-1H-pyrrol-3-yl)benzenesulfonamide;

4-(1-(4-chlorophenyl)-2-cyclopropyl-4-(2-cyclopropylacetyl)-5-methyl-1H-pyrrol-3-yl)benzenesulfonamide;

4-(1-(4-chloro-3-methylphenyl)-4-(2-cyclopropylacetyl)-2,5-dimethyl-1H-pyrrol-3-yl)-2-fluorobenzenesulfonamide;

4-(1-(4-chlorophenyl)-4-(2-cyclopentylacetyl)-2,5-dimethyl-1H-pyrrol-3-yl)benzenesulfonamide;

4-(1-(4-chlorophenyl)-4-(2-cyclopentylacetyl)-2,5-dimethyl-1H-pyrrol-3-yl)-2-fluorobenzenesulfonamide;

4-(1-(4-chlorophenyl)-4-(2-cyclopropylacetyl)-5-ethyl-2-methyl-1H-pyrrol-3-yl)benzenesulfonamide;

4-(1-(4-chlorophenyl)-4-(2-cyclopropylacetyl)-5-methyl-2-(trifluoromethyl)-1H-pyrrol-3-yl) benzenesulfonamide;

4-(1-cyclohexyl-4-(2-cyclopropylacetyl)-2,5-dimethyl-1H-pyrrol-3-yl)benzenesulfonamide;

4-(4-(2-cyclopropylacetyl)-2,5-dimethyl-1-(pyridin-3-yl)-1H-pyrrol-3-yl)benzenesulfonamide; and 4-(4-(2-cyclopropylacetyl)-2,5-dimethyl-1-(1-methylpiperidin-4-yl)-1H-pyrrol-3-yl)benzenesulfonamide.

14. A pharmaceutical composition comprising a compound of claim 1, a tautomer thereof, a stereoisomer thereof, or a pharmaceutically acceptable salt thereof, and a pharmaceutically acceptable carrier.

15. A method of treating a disease, a symptom, or a disorder mediated by nicotinic acetylcholine receptors, said method comprising administering to a subject having said disease, symptom, or disorder a therapeutically effective amount of a compound of claim 1, a tautomer thereof, a stereoisomer thereof, or a pharmaceutically acceptable salt thereof.

16. A method of treating a disease, disorder, or condition mediated by nicotinic acetylcholine receptors in a subject in need thereof, comprising administering to the subject a therapeutically effective amount of a compound of formula (I), a tautomer thereof, a stereoisomer thereof, or a pharmaceutically acceptable salt thereof,

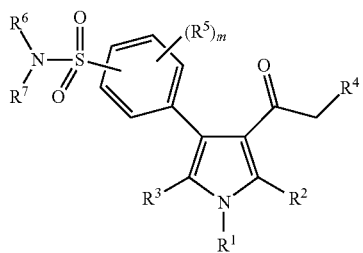

wherein, $R^1$ is selected from substituted- or unsubstituted-cycloalkyl, and substituted- or unsubstituted-aryl, substituted- or unsubstituted-heteroaryl and substituted- or unsubstituted-heterocyclyl;

$R^2$ is selected from substituted- or unsubstituted-alkyl, perhaloalkyl, substituted- or unsubstituted-cycloalkyl, and substituted- or unsubstituted-heterocyclyl;

$R^3$ is selected from substituted- or unsubstituted-alkyl, perhaloalkyl, substituted- or unsubstituted-cycloalkyl, and substituted- or unsubstituted-heterocyclyl;

$R^4$ is selected from substituted- or unsubstituted-cycloalkyl, and substituted- or unsubstituted-heterocyclyl;

$R^5$ is independently selected at each occurrence from halogen, substituted- or unsubstituted-alkyl, perhaloalkyl, substituted- or unsubstituted-cycloalkyl, $-OR^{7b}$, $-NR^6R^7$, and $-C(=O)R^{7a}$; or two $R^5$ groups and the carbon atoms to which they are attached together from 5 to 6 membered carbocycle or 5 to 6 membered heterocycle, the carbocycle or heterocycle is optionally substituted with 1 to 3 substituent(s) independently selected from oxo, halogen, cyano, and alkyl;

$R^6$ and $R^7$ are independently selected from hydrogen, substituted- or unsubstituted-alkyl, substituted- or unsubstituted-cycloalkyl, and $-C(=O)R^7$;

$R^{7a}$ is selected from substituted- or unsubstituted-alkyl, perhaloalkyl, and substituted- or unsubstituted-cycloalkyl;

$R^{7b}$ is selected from hydrogen, substituted- or unsubstituted-alkyl, perhaloalkyl, and substituted- or unsubstituted-cycloalkyl;

m is an integer selected from 0, 1 and 2;

wherein, when the alkyl group is substituted, it is substituted with 1 to 3 substituents independently selected from halogen, perhaloalkyl, cycloalkyl, $-OR^{8b}$, $-N(H)R^8$, and $-N(alkyl)R^8$;

when the cycloalkyl and the carbocycle groups are substituted, each of them is substituted with 1 to 3 substituents independently selected from halogen, alkyl, perhaloalkyl, $-OR^{8b}$, $-N(H)R^8$, and $-N(alkyl)R^8$;

when the aryl group is substituted, it is substituted with 1 to 3 substituents independently selected from halogen, nitro, cyano, hydroxy, alkyl, perhaloalkyl, cycloalkyl, heterocyclyl, $-O$-alkyl, $-O$-perhaloalkyl, $-N(alkyl)$alkyl, $-N(H)$alkyl, $-NH_2$, $-SO_2$-alkyl, $-SO_2$-perhaloalkyl, $-N(alkyl)C(=O)$alkyl, $-N(H)C(=O)$alkyl, $-C(=O)N(alkyl)$alkyl, $-C(=O)N(H)$alkyl, $-C(=O)NH_2$, $-SO_2N(alkyl)$alkyl, $-SO_2N(H)$alkyl, and $-SO_2NH_2$;

when the heteroaryl group is substituted, it is substituted with 1 to 3 substituents independently selected from halogen, nitro, cyano, hydroxy, alkyl, perhaloalkyl, $-O$-alkyl, $-O$-perhaloalkyl, $-N(alkyl)$alkyl, $-N(H)$alkyl, and $-NH_2$;

when the heterocyclyl group is substituted, it can be substituted either on a ring carbon atom(s) or on a ring hetero atom; when it is substituted on a ring carbon atom(s), it is substituted with 1 to 3 substituents independently selected from halogen, nitro, cyano, oxo, alkyl, perhaloalkyl, $OR^{8b}$; and when the 'heterocyclyl' group is substituted on a ring nitrogen, it is substituted with a substituent selected from alkyl, cycloalkyl, $-SO_2$alkyl, and $-C(=O)R^{8a}$;

$R^8$ is selected from hydrogen, alkyl, and cycloalkyl;

$R^{8a}$ is selected from alkyl, perhaloalkyl, and cycloalkyl; and $R^{8b}$ is selected from hydrogen, alkyl, perhaloalkyl, and cycloalkyl.

17. The method of claim 16, wherein the disorder, condition, or disease is selected from Alzheimer's disease, mild cognitive impairment, senile dementia, vascular dementia, dementia of Parkinson's disease, attention deficit disorder, attention deficit hyperactivity disorder, dementia associated with Lewy bodies, AIDS dementia complex, or Pick's disease, dementia associated with Down's syndrome or Huntington's disease, cognitive deficits associated with traumatic brain injury, cognitive decline associated with stroke or poststroke neuroprotection, cognitive and sensorimotor gating deficits associated with schizophrenia, cognitive deficits associated with bipolar disorder, and a cognitive impairment associated with depression, acute pain, post-surgical or postoperative pain, chronic pain, inflammation, inflammatory pain, neuropathic pain, smoking cessation, need for new blood vessel growth associated with wound healing, need for new blood vessel growth associated with vascularization of skin graft or lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, or rheumatoid spondylitis.

18. The method of claim 16, wherein the disease, disorder, or condition is selected from the group classified or diagnosed as major or minor neurocognitive disorders, and disorders arising due to neurodegeneration.

19. The method of claim 16, further comprising administering another medication effective to treat attention deficit hyperactivity disorders, schizophrenia, cognitive disorders, Alzheimer's disease, Parkinson's dementia, vascular dementia or dementia associated with Lewy bodies, or traumatic brain injury.

20. The method of claim 16, further comprising administering an acetylcholinesterase inhibitor, a disease modifying drug or biologic for neurodegenerative disorders, a dopaminergic drug, an antidepressant, or a typical or atypical antipsychotic.

* * * * *